US010655146B2

(12) United States Patent
Esaki et al.

(10) Patent No.: US 10,655,146 B2
(45) Date of Patent: *May 19, 2020

(54) TURKEY HERPESVIRUS VECTORED RECOMBINANT CONTAINING AVIAN INFLUENZA GENES

(71) Applicant: BIOMUNE COMPANY, Lenexa, KS (US)

(72) Inventors: Motoyuki Esaki, Lenexa, KS (US); Lauren Elizabeth Jensen, Kansas City, MO (US); Kristi M. Dorsey, Lenexa, KS (US)

(73) Assignee: BIOMUNE COMPANY, Lenexa, KS (US)

(*) Notice: Subject to any disclaimer, the term of this patent is extended or adjusted under 35 U.S.C. 154(b) by 0 days.

This patent is subject to a terminal disclaimer.

(21) Appl. No.: 16/114,265

(22) Filed: Aug. 28, 2018

(65) Prior Publication Data

US 2018/0363006 A1    Dec. 20, 2018

Related U.S. Application Data

(60) Continuation of application No. 14/551,487, filed on Nov. 24, 2014, now Pat. No. 10,072,272, which is a division of application No. 12/449,037, filed as application No. PCT/US2008/004070 on Mar. 28, 2008, now Pat. No. 8,927,270, which is a continuation-in-part of application No. 11/729,978, filed on Mar. 30, 2007, now abandoned.

(51) Int. Cl.
| | |
|---|---|
| *C12N 15/86* | (2006.01) |
| *C12N 7/00* | (2006.01) |
| *C12N 15/63* | (2006.01) |
| *C12N 15/85* | (2006.01) |
| *C12N 15/869* | (2006.01) |
| *A61K 39/12* | (2006.01) |
| *A61K 39/145* | (2006.01) |
| *C07K 14/005* | (2006.01) |
| *C07K 14/11* | (2006.01) |
| *A61K 39/00* | (2006.01) |

(52) U.S. Cl.
CPC .............. *C12N 15/86* (2013.01); *A61K 39/12* (2013.01); *A61K 39/145* (2013.01); *C07K 14/005* (2013.01); *C07K 14/11* (2013.01); *C12N 7/00* (2013.01); *C12N 15/63* (2013.01); *C12N 15/85* (2013.01); *C12N 15/869* (2013.01); *A61K 2039/5256* (2013.01); *C12N 2710/16143* (2013.01); *C12N 2710/16334* (2013.01); *C12N 2710/16343* (2013.01); *C12N 2710/16443* (2013.01); *C12N 2760/16134* (2013.01); *C12N 2830/34* (2013.01); *C12N 2830/60* (2013.01)

(58) Field of Classification Search
None
See application file for complete search history.

(56) References Cited

U.S. PATENT DOCUMENTS

| 5,965,138 A | 10/1999 | Cochran et al. |
|---|---|---|
| 6,632,664 B1 | 10/2003 | Saitoh et al. |

FOREIGN PATENT DOCUMENTS

| WO | WO 96/05291 | 2/1996 |
|---|---|---|
| WO | WO 2007/022151 | 2/2007 |

OTHER PUBLICATIONS

U.S. Appl. No. 14/551,487, filed Nov. 24, 2014, now allowed.
U.S. Appl. No. 12/449,037, filed Jul. 21, 2009, now U.S. Pat. No. 8,927,270, and.
U.S. Appl. No. 11/729,978, filed Mar. 30, 2007, now abandoned.
Tsukamoto, K. et al. "Complete, Long-Lasting Protection against Lethal Infectious Bursal Disease Virus Challenge by a single Vaccination with an Avian Herpesvirus Vector Expressing VP2 Antigens" Journal of Virology, 2002, pp. 5637-5645, vol. 76, No. 11.
Swayne, D. E. et al. "Influenza" Disease Poultry, 2003, 11th Ed., Chapter 5, Section 1, pp. 135-160.
GenBank Accession No. U79456 (1996).
Luschow et al. "Protection of chickens from lethal avian influenza A virus infection by live-virus vaccination with infectious laryngotracheitis virus recombinants expressing the hemagglutinin (H5) gene" Vaccine, 2001, pp. 4249-4259, vol. 19.
De Marco, M. A. et al., "Long-term Monitoring for Avian Influenza Viruses in Wild Bird Species in Italy" Veterinary Research Communications, Jan. 2003, pp. 107-114, vol. 27, Suppl. 1.
Alexander, D. J. "A review of avian influenza in different bird species" Veterinary Microbiology, May 22, 2000, pp. 3-13, vol. 74, Nos. 1-2.
Esaki, M. et al. "Serological Evaluation of Turkey Herpesvirus Vector Vaccines Expressing the Hemagglutinin Gene of Avian Influenza Virus H5 Subtype under Three Different Promoters" Journal of Poultry Science, 2015, pp. 68-73, vol. 52, No. 1.
Tsukamoto, K. et al. "Complete, Long-Lasting Protection against Lethal Infectious Bursal Disease Virus Challenge by a Single Vaccination with an Avian Herpesvirus Vector Expressing VP2 Antigens" Journal of Virology, Jun. 2002, pp. 5637-5645, vol. 76, No. 11.

(Continued)

Primary Examiner — Nicole Kinsey White
(74) Attorney, Agent, or Firm — Saliwanchik, Lloyd & Eisenschenk

(57) ABSTRACT

The present invention provides a recombinant turkey herpesvirus modified by the presence of the cDNA encoding the hemagglutinin protein of avian influenza virus under a promoter. A poultry vaccine comprising the recombinant turkey herpesvirus described in the present invention can induce serological responses that may be easily detected by the hemagglutination inhibition assay but not by commercially available diagnostic ELISA kits; thus enabling easy differentiation between vaccination and field infection.

4 Claims, 10 Drawing Sheets

Specification includes a Sequence Listing.

(56) References Cited

OTHER PUBLICATIONS

Gamblin, S. J. et al. "Influenza Hemagglutinin and Neuraminidase Membrane Glycoproteins" *The Journal of Biological Chemistry*, Sep. 10, 2010, pp. 28403-28409, vol. 285, No. 37.
Li, Y. et al. "Recombinant herpesvirus of turkeys as a vector-based vaccine against highly pathogenic H7N1 avian influenza and Marek's disease" *Vaccine*, 2011, pp. 8257-8266, vol. 29.
Liu, S. et al. "A Promising Recombinant Herpesvirus of Turkeys Vaccine Expressing PmpD-N of Chlamydia psittaci Based on Elongation Factor-1 Alpha Promoter" *Frontiers in Veterinary Science*, Dec. 14, 2017, pp. 1-6, vol. 4, Article 221.
Kreager, K. S. "Chicken Industry Strategies for Control of Tumor Virus Infections" *Poultry Science*, 1998, pp. 1213-1216, vol. 77.

Construction of the plasmid p45PecH5Wis68

Fig.6

Western blot assay detecting expression of the hemagglutinin protein by the recombinant turkey herpesvirus. Lane 1 = Precision Plus Protein All Blue Standards (Bio-Rad Laboratories, Cat# 161-0373); Lane 2 = CEF control; Lane 3 = HVT FC126 parent strain; Lane 4 = Recombinant HVT with hemagglutinin gene. An arrow indicates the hemagglutinin protein with a molecular weight of 74 kilodalton.

Fig. 7

Hemagglutination inhibition titers in chickens vaccinated with the recombinant turkey herpesvirus with hemagglutinin gene

- Group 1 rHVT/CMVH5Wis68 1638 pfu
- Group 2 rHVT/CMVH5Wis68 375 pfu
- Group 3 rHVT/PecH5Wis68 2800 pfu
- Group 4 rHVT/PecH5Wis68 550 pfu
- Group 5 rHVT/BacH5Wis68 4350 pfu
- Group 6 rHVT/BacH5Wis68 750 pfu
- Group 7 AI H5N9 killed virus (3-weeks-old)
- Group 8 Unvaccinated Controls

Fig. 8

ELISA titers in chickens vaccinated with the recombinant turkey
herpesvirus with hemagglutinin gene using a commercial ELISA kit
(Idexx Laboratories, FlockCheck AIV)

S/P Value* = S/P Values of equal to or greater than 0.5 are considered positive.

Group 1   rHVT/CMVH5Wis68 1638 pfu
Group 2   rHVT/CMVH5Wis68 375 pfu
Group 3   AI H5N9 killed virus (3-weeks-old)
Group 4   Unvaccinated Controls

Fig.9

ELISA titers in chickens vaccinated with the recombinant turkey herpesvirus with hemagglutinin gene using a commercial ELISA kit (Synbiotics, ProFLOK AIV Ab test kit)

ELISA titers* = ELISA titers of equal to or greater than 570 are considered positive.

Group 1    rHVT/CMVH5Wis68 1638 pfu
Group 2    rHVT/CMVH5Wis68 375 pfu
Group 3    AI H5N9 killed virus (3-weeks-old)
Group 4    Unvaccinated Controls

Fig.10

Hemagglutination inhibition titers in chickens vaccinated with the recombinant turkey herpesvirus with hemagglutinin gene (second trial)

―○― Group 1 rHVT/CMVH5Wis68 in ovo
―□― Group 2 rHVT/CMVH5Wis68 subcutaneous
―●― Group 3 rHVT/BacH5Wis68 subcutaneous
―■― Group 4 Unvaccinated Controls

SEQUENCE LISTING

<160> NUMBER OF SEQ ID NOS: 25

<210> SEQ ID NO 1
<211> LENGTH: 1695
<212> TYPE: DNA
<213> ORGANISM: Influenza A virus
<220> FEATURE:
<221> NAME/KEY: CDS
<222> LOCATION: (1)..(1695)
<223> OTHER INFORMATION: Hemagglutinin gene of A/Turkey/Wisconsin/68 (H5N9)

<400> SEQUENCE: 1

```
atg gaa aga ata gtg att gcc ctt gca ata atc agc gtt gtc aaa ggt      48
Met Glu Arg Ile Val Ile Ala Leu Ala Ile Ile Ser Val Val Lys Gly
1               5                   10                  15 gac caa atc tgc atc ggt tat cat gca aac aat tca aca aaa caa gtt      96
Asp Gln Ile Cys Ile Gly Tyr His Ala Asn Asn Ser Thr Lys Gln Val
            20                  25                  30 gac aca atc atg gag aag aat gtg acg gtc aca cat gct caa gat ata     144
Asp Thr Ile Met Glu Lys Asn Val Thr Val Thr His Ala Gln Asp Ile
        35                  40                  45 ctg gaa aaa gag cac aac ggg aaa ctc tgc agt ctc aaa gga gtg agg     192
Leu Glu Lys Glu His Asn Gly Lys Leu Cys Ser Leu Lys Gly Val Arg
    50                  55                  60 ccc ctc att ctg aag gat tgc agt gtg gct gga tgg ctt ctt ggg aac     240
Pro Leu Ile Leu Lys Asp Cys Ser Val Ala Gly Trp Leu Leu Gly Asn
65                  70                  75                  80 cca atg tgt gat gag ttc cta aat gta ccg gaa tgg tca tat att gta     288
Pro Met Cys Asp Glu Phe Leu Asn Val Pro Glu Trp Ser Tyr Ile Val
                85                  90                  95 gag aag gac aat cca acc aat ggc tta tgt tat ccg gga gac ttc aat     336
Glu Lys Asp Asn Pro Thr Asn Gly Leu Cys Tyr Pro Gly Asp Phe Asn
            100                 105                 110 gat tat gaa gaa ctg aag tat tta atg agc aac aca aac cat ttt gag     384
```

```
                Asp Tyr Glu Glu Leu Lys Tyr Leu Met Ser Asn Thr Asn His Phe Glu
                        115                 120                 125 aaa att caa ata atc cct agg aac tct tgg tcc aat cat gat gcc tca            432
Lys Ile Gln Ile Ile Pro Arg Asn Ser Trp Ser Asn His Asp Ala Ser
            130                 135                 140 tca gga gtg agc tca gca tgc cca tac aat ggt aga tct tcc ttt ttc            480
Ser Gly Val Ser Ser Ala Cys Pro Tyr Asn Gly Arg Ser Ser Phe Phe
145                 150                 155                 160 agg aat gtg gtg tgg ttg atc aag aag agt aat gca tac cca aca ata            528
Arg Asn Val Val Trp Leu Ile Lys Lys Ser Asn Ala Tyr Pro Thr Ile
                165                 170                 175 aag agg acc tac aat aac acc aat gta gag gac ctt ctg ata ttg tgg            576
Lys Arg Thr Tyr Asn Asn Thr Asn Val Glu Asp Leu Leu Ile Leu Trp
            180                 185                 190 gga atc cat cac cct aat gat gca gcg gaa caa acg gaa ctc tat cag            624
Gly Ile His His Pro Asn Asp Ala Ala Glu Gln Thr Glu Leu Tyr Gln
        195                 200                 205 aac tcg aac act tat gtg tct gta gga aca tca aca cta aat cag agg            672
Asn Ser Asn Thr Tyr Val Ser Val Gly Thr Ser Thr Leu Asn Gln Arg
    210                 215                 220 tca att cca gaa ata gct acc agg ccc aaa gtg aat gga caa agt gga            720
Ser Ile Pro Glu Ile Ala Thr Arg Pro Lys Val Asn Gly Gln Ser Gly
225                 230                 235                 240 aga ata gaa ttt ttc tgg aca ata cta agg ccg aac gat gca atc agc            768
Arg Ile Glu Phe Phe Trp Thr Ile Leu Arg Pro Asn Asp Ala Ile Ser
                245                 250                 255 ttt gaa agt aat ggg aac ttt ata gct cct gaa tat gca tac aag ata            816
Phe Glu Ser Asn Gly Asn Phe Ile Ala Pro Glu Tyr Ala Tyr Lys Ile
            260                 265                 270 gtt aaa aag gga gat tca gca atc atg aga agc gaa ctg gag tat ggc            864
Val Lys Lys Gly Asp Ser Ala Ile Met Arg Ser Glu Leu Glu Tyr Gly
        275                 280                 285 aac tgt gat acc aaa tgt cag acc cca gtg ggt gct ata aat tcc agt            912
Asn Cys Asp Thr Lys Cys Gln Thr Pro Val Gly Ala Ile Asn Ser Ser
    290                 295                 300 atg cct ttt cac aat gtt cat ccc ctt acc att gga gag tgt ccc aaa            960
Met Pro Phe His Asn Val His Pro Leu Thr Ile Gly Glu Cys Pro Lys
305                 310                 315                 320 tat gtc aaa tca gat aaa ctg gtc ctt gca aca gga ctg agg aac gtg           1008
Tyr Val Lys Ser Asp Lys Leu Val Leu Ala Thr Gly Leu Arg Asn Val
                325                 330                 335 cct cag aga gaa aca aga ggt ctg ttt gga gca ata gca gga ttc ata           1056
Pro Gln Arg Glu Thr Arg Gly Leu Phe Gly Ala Ile Ala Gly Phe Ile
            340                 345                 350 gaa ggg ggg tgg caa gga atg gta gat gga tgg tat ggt tac cat cat           1104
Glu Gly Gly Trp Gln Gly Met Val Asp Gly Trp Tyr Gly Tyr His His
        355                 360                 365 agc aac gag cag gga agt gga tat gct gca gac aaa gag tcc act cag           1152
Ser Asn Glu Gln Gly Ser Gly Tyr Ala Ala Asp Lys Glu Ser Thr Gln
    370                 375                 380 aaa gca atc gac ggg atc acc aat aaa gtc aac tca atc att gac aaa           1200
Lys Ala Ile Asp Gly Ile Thr Asn Lys Val Asn Ser Ile Ile Asp Lys
385                 390                 395                 400 atg aac act caa ttc gaa gcc gtt ggg aaa gaa ttc aac aac tta gaa           1248
Met Asn Thr Gln Phe Glu Ala Val Gly Lys Glu Phe Asn Asn Leu Glu
                405                 410                 415 agg aga ata gaa aat ttg aat aag aaa atg gaa gat gga ttt cta gat           1296
Arg Arg Ile Glu Asn Leu Asn Lys Lys Met Glu Asp Gly Phe Leu Asp
            420                 425                 430
```

```
gta tgg act tac aat gca gaa ctt ctg gtg ctc atg gaa aat gaa aga    1344
Val Trp Thr Tyr Asn Ala Glu Leu Leu Val Leu Met Glu Asn Glu Arg
    435             440             445 act ctg gat ttc cat gat tca tat gtc aag aac cta tac gat aag gtc    1392
Thr Leu Asp Phe His Asp Ser Tyr Val Lys Asn Leu Tyr Asp Lys Val
450             455             460 cga ctc cag ctg aga gat aat gca aaa gaa ttg ggc aat ggg tgt ttt    1440
Arg Leu Gln Leu Arg Asp Asn Ala Lys Glu Leu Gly Asn Gly Cys Phe
465             470             475             480 gag ttc tac cac aaa tgt gac aat gaa tgc atg gaa agt gtg aga aac    1488
Glu Phe Tyr His Lys Cys Asp Asn Glu Cys Met Glu Ser Val Arg Asn
            485             490             495 gga acg tat gac tat cca caa tac tca gaa gaa tca agg ctg aac aga    1536
Gly Thr Tyr Asp Tyr Pro Gln Tyr Ser Glu Glu Ser Arg Leu Asn Arg
        500             505             510 gag gaa ata gat gga gtc aaa ttg gag tca atg ggc acc tat cag ata    1584
Glu Glu Ile Asp Gly Val Lys Leu Glu Ser Met Gly Thr Tyr Gln Ile
    515             520             525 cta tca atc tac tca aca gtg gcg agt tcc cta gca ctg gca atc atg    1632
Leu Ser Ile Tyr Ser Thr Val Ala Ser Ser Leu Ala Leu Ala Ile Met
530             535             540 gta gct ggt ctg tct ttt tgg atg tgc tcc aat gga tca ttg cag tgc    1680
Val Ala Gly Leu Ser Phe Trp Met Cys Ser Asn Gly Ser Leu Gln Cys
545             550             555             560 aga att tgc atc tag                                                1695
Arg Ile Cys Ile <210> SEQ ID NO 2
<211> LENGTH: 564
<212> TYPE: PRT
<213> ORGANISM: Influenza A virus

<400> SEQUENCE: 2

Met Glu Arg Ile Val Ile Ala Leu Ala Ile Ile Ser Val Val Lys Gly
1               5                   10                  15

Asp Gln Ile Cys Ile Gly Tyr His Ala Asn Asn Ser Thr Lys Gln Val
            20                  25                  30

Asp Thr Ile Met Glu Lys Asn Val Thr Val Thr His Ala Gln Asp Ile
        35                  40                  45

Leu Glu Lys Glu His Asn Gly Lys Leu Cys Ser Leu Lys Gly Val Arg
    50                  55                  60

Pro Leu Ile Leu Lys Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Asp Asn Pro Thr Asn Gly Leu Cys Tyr Pro Gly Asp Phe Asn
            100                 105                 110

Asp Tyr Glu Glu Leu Lys Tyr Leu Met Ser Asn Thr Asn His Phe Glu
        115                 120                 125

Lys Ile Gln Ile Ile Pro Arg Asn Ser Trp Ser Asn His Asp Ala Ser
    130                 135                 140

Ser Gly Val Ser Ser Ala Cys Pro Tyr Asn Gly Arg Ser Ser Phe Phe
145                 150                 155                 160

Arg Asn Val Val Trp Leu Ile Lys Lys Ser Asn Ala Tyr Pro Thr Ile
                165                 170                 175

Lys Arg Thr Tyr Asn Asn Thr Asn Val Glu Asp Leu Leu Ile Leu Trp
            180                 185                 190
```

```
Gly Ile His His Pro Asn Asp Ala Ala Glu Gln Thr Glu Leu Tyr Gln
            195                 200                 205

Asn Ser Asn Thr Tyr Val Ser Val Gly Thr Ser Thr Leu Asn Gln Arg
        210                 215                 220

Ser Ile Pro Glu Ile Ala Thr Arg Pro Lys Val Asn Gly Gln Ser Gly
225                 230                 235                 240

Arg Ile Glu Phe Phe Trp Thr Ile Leu Arg Pro Asn Asp Ala Ile Ser
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Arg Ser Glu Leu Glu Tyr Gly
        275                 280                 285

Asn Cys Asp Thr Lys Cys Gln Thr Pro Val Gly Ala Ile Asn Ser Ser
290                 295                 300

Met Pro Phe His Asn Val His Pro Leu Thr Ile Gly Glu Cys Pro Lys
305                 310                 315                 320

Tyr Val Lys Ser Asp Lys Leu Val Leu Ala Thr Gly Leu Arg Asn Val
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
370                 375                 380

Lys Ala Ile Asp Gly Ile Thr Asn Lys Val Asn Ser Ile Ile Asp Lys
385                 390                 395                 400

Met Asn Thr Gln Phe Glu Ala Val Gly Lys Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Tyr Val Lys Asn Leu Tyr Asp Lys Val
450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ser Arg Leu Asn Arg
            500                 505                 510

Glu Glu Ile Asp Gly Val Lys Leu Glu Ser Met Gly Thr Tyr Gln Ile
        515                 520                 525

Leu Ser Ile Tyr Ser Thr Val Ala Ser Ser Leu Ala Leu Ala Ile Met
530                 535                 540

Val Ala Gly Leu Ser Phe Trp Met Cys Ser Asn Gly Ser Leu Gln Cys
545                 550                 555                 560

Arg Ile Cys Ile

<210> SEQ ID NO 3
<211> LENGTH: 587
<212> TYPE: DNA
<213> ORGANISM: Cytomegalovirus
<220> FEATURE:
<221> NAME/KEY: promoter
<222> LOCATION: (1)..(587)
```

-continued

<223> OTHER INFORMATION: Cytomegalovirus immediate early promoter

<400> SEQUENCE: 3

```
agttattaat agtaatcaat tacggggtca ttagttcata gcccatatat ggagttccgc      60
gttacataac ttacggtaaa tggcccgccg gctgaccgcc caacgacccc cgcccattga     120
cgtcaataat gacgtatgtt cccatagtaa cgccaatagg gactttccat tgacgtcaat     180
gggtggagta tttacggtaa actgcccatt ggcagtacat caagtgtatc atatgccaag     240
tacgccccct attgacgtca atgacggtaa atggcgcgcc tggcattatg cccagtacat     300
gaccttatgg gactttccta cttggcagta catctacgta ttagtcatcg ctattaccat     360
ggtgatgcgg ttttggcagt acatcaatgg gcgtggatag cggtttgact cacggggatt     420
tccaagtctc cacccccattg acgtcaatgg gagtttgttt tggcaccaaa atcaacggga     480
ctttccaaaa tgtcgtaaca actccgcccc attgacgcaa atgggcggta ggcgtgtacg     540
gtgggaggtc tatataagca gagctggttt agtgaaccgt cagatcc                   587
```

<210> SEQ ID NO 4
<211> LENGTH: 29
<212> TYPE: DNA
<213> ORGANISM: Artificial
<220> FEATURE:
<223> OTHER INFORMATION: synthetic primer for DNA for PCR

<400> SEQUENCE: 4

```
tgacggatcc atggaaagaa tagtgattg                                        29
```

<210> SEQ ID NO 5
<211> LENGTH: 29
<212> TYPE: DNA
<213> ORGANISM: Artificial
<220> FEATURE:
<223> OTHER INFORMATION: synthetic primer for DNA for PCR

<400> SEQUENCE: 5

```
ctgacagtcg acctagatgc aaattctgc                                        29
```

<210> SEQ ID NO 6
<211> LENGTH: 17
<212> TYPE: DNA
<213> ORGANISM: Artificial
<220> FEATURE:
<223> OTHER INFORMATION: synthetic primer for DNA for PCR

<400> SEQUENCE: 6

```
gtaaaacgac ggccagt                                                     17
```

<210> SEQ ID NO 7
<211> LENGTH: 19
<212> TYPE: DNA
<213> ORGANISM: Artificial
<220> FEATURE:
<223> OTHER INFORMATION: synthetic primer DNA for PCR

<400> SEQUENCE: 7

```
ggaaacagct atgaccatg                                                   19
```

<210> SEQ ID NO 8
<211> LENGTH: 25
<212> TYPE: DNA
<213> ORGANISM: Artificial
<220> FEATURE:
<223> OTHER INFORMATION: synthetic primer DNA for PCR

<400> SEQUENCE: 8
ctggacaata ctaaggccga acgat                                          25

<210> SEQ ID NO 9
<211> LENGTH: 22
<212> TYPE: DNA
<213> ORGANISM: Artificial
<220> FEATURE:
<223> OTHER INFORMATION: synthetic primer DNA for PCR

<400> SEQUENCE: 9
cactggggtc tgacatttgg ta                                             22

<210> SEQ ID NO 10
<211> LENGTH: 30
<212> TYPE: DNA
<213> ORGANISM: Artificial
<220> FEATURE:
<223> OTHER INFORMATION: synthetic primer DNA for PCR

<400> SEQUENCE: 10
gggctgcaga gttattaata gtaatcaatt                                     30

<210> SEQ ID NO 11
<211> LENGTH: 25
<212> TYPE: DNA
<213> ORGANISM: Artificial
<220> FEATURE:
<223> OTHER INFORMATION: synthetic primer DNA for PCR

<400> SEQUENCE: 11
cgcgccattt accgtcattg acgtc                                          25

<210> SEQ ID NO 12
<211> LENGTH: 25
<212> TYPE: DNA
<213> ORGANISM: Artificial
<220> FEATURE:
<223> OTHER INFORMATION: synthetic primer DNA for PCR

<400> SEQUENCE: 12
gggtcgttgg gcggtcagcc ggcgg                                          25

<210> SEQ ID NO 13
<211> LENGTH: 25
<212> TYPE: DNA
<213> ORGANISM: Artificial
<220> FEATURE:
<223> OTHER INFORMATION: synthetic primer DNA for PCR

<400> SEQUENCE: 13
cttacggtaa atggcccgcc ggctg                                          25

<210> SEQ ID NO 14
<211> LENGTH: 25
<212> TYPE: DNA
<213> ORGANISM: Artificial
<220> FEATURE:
<223> OTHER INFORMATION: synthetic primer DNA for PCR

<400> SEQUENCE: 14
tacacttgat gtactgccaa tgggc                                          25

<210> SEQ ID NO 15

```
<211> LENGTH: 25
<212> TYPE: DNA
<213> ORGANISM: Artificial
<220> FEATURE:
<223> OTHER INFORMATION: synthetic primer DNA for PCR

<400> SEQUENCE: 15
tatttacggt aaactgccca ttggc                                    25

<210> SEQ ID NO 16
<211> LENGTH: 30
<212> TYPE: DNA
<213> ORGANISM: Artificial
<220> FEATURE:
<223> OTHER INFORMATION: synthetic primer DNA for PCR

<400> SEQUENCE: 16
acgtcaatga cggtaaatgg cgcgcctggc                               30

<210> SEQ ID NO 17
<211> LENGTH: 30
<212> TYPE: DNA
<213> ORGANISM: Artificial
<220> FEATURE:
<223> OTHER INFORMATION: synthetic primer DNA for PCR

<400> SEQUENCE: 17
cgtctagagg atctgacggt tcactaaacc                               30

<210> SEQ ID NO 18
<211> LENGTH: 33
<212> TYPE: DNA
<213> ORGANISM: Artificial
<220> FEATURE:
<223> OTHER INFORMATION: synthetic primer DNA for PCR

<400> SEQUENCE: 18
tgtggtaccg tcgacgattc acagtcccaa ggc                           33

<210> SEQ ID NO 19
<211> LENGTH: 33
<212> TYPE: DNA
<213> ORGANISM: Artificial
<220> FEATURE:
<223> OTHER INFORMATION: synthetic primer DNA for PCR

<400> SEQUENCE: 19
cttggcctta ttggcctaag atacattgat gag                           33

<210> SEQ ID NO 20
<211> LENGTH: 39
<212> TYPE: DNA
<213> ORGANISM: Artificial
<220> FEATURE:
<223> OTHER INFORMATION: synthetic primer DNA for PCR

<400> SEQUENCE: 20
cagtgtcgct gcagctcagt gcatgcacgc tcattgccc                     39

<210> SEQ ID NO 21
<211> LENGTH: 49
<212> TYPE: DNA
<213> ORGANISM: Artificial
<220> FEATURE:
<223> OTHER INFORMATION: synthetic primer DNA for PCR

<400> SEQUENCE: 21
```

-continued

```
gctctagagg cgtggagctt gggggctgcg gaggaacaga gaagggaag          49
```

<210> SEQ ID NO 22
<211> LENGTH: 17
<212> TYPE: DNA
<213> ORGANISM: Artificial
<220> FEATURE:
<223> OTHER INFORMATION: synthetic primer DNA for PCR

<400> SEQUENCE: 22

```
gggggtggca aggaatg                                             17
```

<210> SEQ ID NO 23
<211> LENGTH: 20
<212> TYPE: DNA
<213> ORGANISM: Artificial
<220> FEATURE:
<223> OTHER INFORMATION: synthetic primer DNA for PCR

<400> SEQUENCE: 23

```
gctagggaac tcgccactgt                                          20
```

<210> SEQ ID NO 24
<211> LENGTH: 24
<212> TYPE: DNA
<213> ORGANISM: Artificial
<220> FEATURE:
<223> OTHER INFORMATION: synthetic primer DNA for PCR

<400> SEQUENCE: 24

```
tagcggcacg gaaacagata gaga                                     24
```

<210> SEQ ID NO 25
<211> LENGTH: 24
<212> TYPE: DNA
<213> ORGANISM: Artificial
<220> FEATURE:
<223> OTHER INFORMATION: synthetic primer DNA for PCR

<400> SEQUENCE: 25

```
tggcgatacg gttcctggtt tgac                                     24
```

TURKEY HERPESVIRUS VECTORED RECOMBINANT CONTAINING AVIAN INFLUENZA GENES

CROSS-REFERENCE TO RELATED APPLICATIONS

This application is a continuation of U.S. Ser. No. 14/551,487, filed Nov. 24, 2014, now U.S. Pat. No. 10,072,272, which is a divisional of U.S. Ser. No. 12/449,037, filed Jul. 21, 2009, now U.S. Pat. No. 8,927,270, which is the U.S. national stage application of International Patent Application No. PCT/US2008/004070, filed Mar. 28, 2008, which is a continuation in part of U.S. Ser. No. 11/729,978, filed Mar. 30, 2007, now abandoned.

BACKGROUND OF THE INVENTION

1. Field of the Invention

The present invention relates generally to avian vaccines against avian influenza (AI). More specifically, the present invention provides a recombinant turkey herpesvirus modified by the presence of the cDNA encoding the hemagglutinin (HA) protein of avian influenza virus under a promoter.

2. Description of the Related Art

Avian influenza is caused by avian influenza viruses that are classified in the family Orthomyxoviridae, genus Influenzavirus A. The genome of the avian influenza virus consists of eight segments of single-stranded, negative-sense RNA. The viral genome encodes ten proteins, of which eight proteins are structural proteins including HA and neuraminidase (NA), and two proteins are nonstructural. Influenza A viruses are divided into subtypes based on antigenicity of HA and NA proteins. There are 16 HA antigens and nine NA antigens recognized. HA is considered the major antigen that can elicit protective antibodies in birds.

Influenza A viruses from poultry are categorized into two pathotypes based on their pathogenicity: highly pathogenic avian influenza (HPAI) viruses and low pathogenic avian influenza (LPAI) viruses. Most avian influenza viruses are of low virulence, but a few viruses of H5 and H7 subtypes can cause severe systemic disease that results in high mortality. Although only a few H5 and H7 avian influenza viruses are of high virulence, all H5 and H7 viruses are identified as notifiable avian influenza virus by World Organization for Animal Health (OIE) because of the risk of low virulent viruses increasing virulence by mutation.

Since the late 1990s, there has been a significant increase in the number of AI outbreaks and in the number of birds involved in those outbreaks (I. Capua et al., 2004, Avian Pathology, 33: 393-404). The most notable example is a series of H5N1 HPAI outbreaks in China and South-East Asia, which has now spread to other parts of the world such as Europe, the Middle East, and Africa. The outbreaks have cost as many as 160 human lives in more than 10 countries since 2003 although apparent human-to-human transmission has yet to be confirmed. These recent outbreaks have caused tremendous economic losses to the poultry industry and raised public concerns because of fear of a possible human pandemic.

Vaccination against AI had not been conducted extensively until recently because the so-called "stamping-out" procedure has been the primary option. In the "stamping-out" procedure, all chickens in flocks infected with AI are culled. Most AI outbreaks were eradicated or controlled by "stamping-out" in the past. However, in recent AI outbreaks, especially in the H5N1 outbreaks, there have been situations in which massive culling was not practical or feasible due to intolerable economic costs and losses associated with the culling, widespread presence of so-called backyard chickens, and so forth. In those situations, vaccination has been considered a suitable and powerful tool to support AI eradication or AI control programs because vaccination has been shown to protect poultry against clinical signs and death and reduce virus shedding in vaccinated birds, thereby reducing transmission of virus (D. E. Swayne., 2003, Developments in Biologicals, 114: 201-212). In order to utilize vaccines in AI eradication programs or AI control programs, it is critical for trade and surveillance purposes that vaccinated birds may be differentiated from those infected with the field virus. In fact, field exposure in vaccinated flocks must be detected in simple serological assays. Otherwise, the field virus may circulate in the vaccinated birds undetected. It is also important that evidence of vaccination may be detected by simple assays in order to confirm that most or all birds in vaccinated flocks are properly vaccinated.

Commercial vaccines currently available are inactivated whole AI antigens with oil adjuvant and a fowlpox virus vectored recombinant vaccine. Although both vaccines have been shown to be efficacious, they require labor-intensive and expensive parenteral vaccination that involves handling each bird manually. While the inactivated AI vaccines have been used in the program called DIVA ("Differentiation of infected from vaccinated animals"), there have been no commercially available tests developed for mass application. It has been shown that chickens pre-immunized with fowlpox virus either by field exposure or by vaccination with conventional fowlpox vaccines would not develop consistent protective immunity against AI after vaccinated with the fowlpox virus vectored recombinant AI vaccine (D. E. Swayne et al., 2000, Avian Diseases, 44: 132-137). The fowlpox virus vectored recombinant AI vaccine has failed to elicit serological response detectable by the hemagglutination inhibition (HI) test consistently (D. E. Swayne et al., 1997, Avian Diseases, 41: 910-922). Hence, development of vaccines that are easier to administer and that may be readily differentiated from field virus infection is desirable for the poultry industry.

The commercial fowlpox virus vectored recombinant AI vaccine contains the HA gene of the AI virus A/turkey/Ireland/1378/83 (H5N8) (J. R. Taylor et al., 1988, Vaccine, 6: 504-508). Several other experimental fowlpox vectored recombinant vaccines have been developed and shown to be efficacious against challenge with AI viruses in experimental conditions. Avian influenza virus genes contained in the fowlpox vectored recombinant vaccines include the HA gene from A/Chicken/Scotland/59 (H5N1) (C. W. Beard et al., 1991, Avian Diseases, 35: 356-359) and the HA and NA genes from A/Goose/Guangdond/3/96 (H5N1) (C. Qiao et al., 2003, Avian Pathol., 32:25-31). M. Mingxiao et al. fused the HA genes from H5N1 subtype and H7N1 subtype to form a single open frame and inserted into a recombinant fowlpox virus along with chicken Interleukin-18 (M. Mingxiao et al., 2006, Vaccine, 24: 4304-4311). Broad cross protection among the AI virus H5 subtypes has been observed. The fowlpox virus vectored recombinant AI vaccine and the inactivated whole AI vaccines for avian influenza H5 subtypes have been demonstrated to protect chickens against challenge with diverse H5 subtype AI viruses, of which deduced HA amino acid sequence similarities with the vaccines are as low as 87% (D. E. Swayne et al., 2000, Veterinary Microbiol., 74: 165-172).

Next generation vaccines under development include recombinant Newcastle disease virus vaccines (D. E.

Swayne et al., 2003, Avian Diseases, 47: 1047-1050; J. Veits et al., 2006, Proc. Natl. Acad. Sci. U.S.A., 103:8197-8202; M. Park et al., 2006, Proc. Natl. Acad. Sci. U.S.A., 103: 8203-8208; and J. Ge et al., 2007, J. Virol. 81: 150-158), recombinant infectious laryngotracheitis virus vaccines (D. Luschow et al., 2001, Vaccine 19: 4249-4259 and J. Veits et al., 2003, J. Gen. Virol. 84: 3343-3352), a recombinant adenovirus vaccine (W. Gao et al., 2006, J. Virol. 80: 1959-1964), baculovirus-expressed subunit vaccines (J. Crawford et al., 1999, Vaccine, 17:2265-2274 and D. E. Swayne et al., 2001, Avian Diseases, 45: 355-365) and DNA vaccines (U.S. Pat. No. 5,916,879 and M. Cherbonnel et al., 2003, Avian Diseases, 47: 1181-1186). Although the recombinant Newcastle disease virus vaccines, the recombinant infectious laryngotracheitis virus vaccines, and the recombinant adenovirus vaccine were able to confer partial to semi-complete protection against AI challenge in specific pathogen free chickens, their efficacy in chickens with maternal antibodies to the vector viruses or AI, or in chickens with previous infection or vaccination with the vector viruses remains to be demonstrated. The DNA vaccines have also shown to provide protective immunity in chickens, but they require at least two vaccinations and individual administration to each chicken. The baculovirus-expressed subunit vaccines also require individual administration to each chicken.

Turkey herpesvirus (HVT), Marek's disease virus (MDV) serotype-3, has been used as a vector to express antigens from avian pathogens. Wild type HVT or recombinant HVT can be administered to either the late developmental stage of embryos via the in ovo route or one-day-old chicks via the subcutaneous route at hatcheries. Recombinant, cell-associated HVT vaccines, after inoculation into embryos or one-day-old chicks with maternal antibodies to inserted antigens, are demonstrated to be able to overcome influences of maternal antibodies and confer protective immunity to chickens as maternal antibodies wane (U.S. Pat. Nos. 6,764, 684 and 6,866,852). Excellent duration of immunity is also achieved by recombinant HVT (U.S. Pat. No. 6,866,852) probably because HVT goes latent and stays inside vaccinated birds for their whole life. Thus, HVT may be considered an excellent vector for avian pathogens. There have been no reports of constructing recombinant HVT or MDV with avian influenza antigens. Although claim 15 of U.S. Pat. No. 5,853,733 describes the recombinant HVT comprising a polypeptide gene of AI virus inserted within a region which corresponds to an EcoRI #9 fragment of the HVT genome, there is no actual example of constructing recombinant HVT with avian influenza antigens. In mammalian species, U.S. Pat. No. 6,225,111 describes construction of recombinant equine herpesviruses containing the HA gene of equine influenza virus, but there is no data about vaccine efficacy of these recombinants.

BRIEF DESCRIPTION OF THE INVENTION

The present invention provides a recombinant HVT modified by the presence of the cDNA encoding the HA protein of avian influenza virus under a promoter. The recombinant HVT is able to elicit a serological response that is easily detected by the HI assay but not by commercially available diagnostic ELISA kits. This feature of the recombinant virus enables easy differentiation between vaccination and field infection. A poultry vaccine comprising the recombinant HVT is also provided.

The present invention is described below in more detail.
(Avian Influenza Virus Hemagglutinin Gene)

The hemagglutinin gene may be obtained from any subtype or any strain of avian influenza virus. Preferably, the HA gene is obtained from an avian influenza virus of the H5 subtype. More preferably, the HA gene is obtained from avian influenza virus of the H5N9 subtype. Most preferably, the HA gene is obtained from the avian influenza virus A/Turkey/Wisconsin/68 (H5N9) strain. A nucleotide sequence of the HA gene from the A/Turkey/Wisconsin/68 (H5N9) strain is shown in SEQ ID NO: 1. The sequence in SEQ ID NO: 1 differs from the published nucleotide sequence of the HA gene of the A/Turkey/Wisconsin/68 (H5N9) strain (M. Garcia et al., 1997, Virus Res. 51: 115-124, GenBank Accession # U79456) by several bases. These differences are probably due to the genetically unstable nature of avian influenza viruses, which have an RNA genome. Therefore, the sequence shown in SEQ ID NO: 1 is only an example and the present invention should not be restricted to the sequence.
(Promoter)

Adjacent to the HA gene in an HVT genome, typically at the 5' region of the HA gene, a regulatory DNA sequence, which is referred to here as a promoter, is included in order to control transcription of the HA gene, and thereby to control expression of the HA gene (generation of the HA protein). When transcription and thereby expression of a gene is controlled by a promoter, the gene is considered under control of the promoter. In the present invention, the HA gene is under control of the cytomegalovirus immediate early promoter (CMV promoter). We found that recombinant HVT with the HA gene in combination with the CMV promoter was capable of conferring higher and more uniform serology titers by HI in chickens than the recombinant HVT with other promoters such as the chicken beta-actin promoter (T. A. Kost et al., 1983, Nucleic Acids Res. 11:8287-8301) and a modified chicken beta-actin promoter (U.S. Pat. No. 6,866,852). A nucleotide sequence of the CMV promoter is described in the literature (M. Boshart et al., 1985, Cell 41: 521-530, GenBank Accession # K03104). However, as long as a promoter is functional in cells or in the bodies of avian species, the nucleotide sequence of a promoter does not have to be identical to the sequence in the literature. The CMV promoter, the sequence of which is shown in SEQ ID NO: 3, is slightly modified from the original sequence by the inventors, but was demonstrated to express the HA gene effectively.
(Turkey Herpesvirus)

Turkey herpesvirus is a double-stranded linear DNA virus in the Herpesviridae family and Alphaherpesvirinae subfamily. HVT is ubiquitous and non-oncogenic in domestic turkeys and it is classified as serotype 3 of Marek's disease virus. Vaccination of chickens with HVT has been extensively conducted to prevent Marek's disease in chickens. As long as it is non-pathogenic to chickens, any HVT can be used in the present invention. For instance, the following HVT strains, FC126, PB-THV1, H-2, YT-7, WTHV-1, and HPRS-26, are suitable for the backbone virus. Among these, the FC126 strain is favorable for use in the present invention.
(Region for Gene Insertion)

In the present invention, the HA gene and the CMV promoter are inserted into an HVT DNA genome. Preferably, the HA gene and the CMV promoter are inserted into a region in the HVT genome that is not essential for virus growth, which is referred to here as a non-essential region. In other words, a non-essential region may be defined as a region where modification or insertion of a foreign gene does not prevent the virus from replicating successfully in vitro or in vivo. Several non-essential regions in the HVT genome have been reported. For instance, the HA gene and the CMV promoter can be inserted into, but not limited to UL43 (WO 89/01040), US2 (WO 93/25665) or inter-ORF region between UL44 and UL46 (WO 99/18215). Most preferably, the HA gene and the CMV promoter are inserted into the inter-ORF region between UL45 and UL46.

For the present invention, a non-essential region may be newly identified by the following general procedure. First, HVT DNA fragments of appropriate lengths are cloned into an E. coli plasmid and physically mapped by restriction enzyme analysis. Then, a gene cassette consisting of a promoter and a marker gene is inserted into an appropriate restriction site of the cloned DNA fragment resulting in a homology plasmid. If homologous recombination with the obtained homology plasmid results in a recombinant virus expressing the inserted marker gene and if the virus is stable in vitro and in vivo, the originally selected DNA fragment should be a non-essential region suitable for HA gene and CMV promoter insertion.

(Construction of rHVT)

For the present invention, any known method of generating recombinant HVT is applicable. A typical example is as follows. (1) First, as described above, a recombinant plasmid that contains a non-essential region of the HVT genome is constructed. Then, preferably with a promoter at the 5' terminus and a polyadenylation signal at the 3' terminus, the HA gene is inserted into the non-essential region to generate a homology plasmid. (2) The homology plasmid is transfected into chicken embryo fibroblast (CEF) cells infected with parent HVT or co-transfected into CEF cells with infectious HVT genomic DNA. Transfection can be performed by any known method. (3) The transfected CEF cells are planted on tissue culture plates and incubated until virus plaques become visible. (4) The identifiable plaques include recombinant virus as well as parent wild-type virus. The recombinant virus may be purified from wild type virus by any known method to detect expression of inserted foreign genes.

(Avian Influenza-Marek's Disease Bivalent Vaccine)

Since the HA protein is a protective antigen of avian influenza virus and the backbone HVT is a live Marek's disease vaccine, the recombinant HVT containing the HA gene in the present invention may be used as a bivalent vaccine against AI and Marek's disease or as a monovalent vaccine against AI.

The vaccine, consisting mainly of the recombinant HVT in the present invention, may also include avian cells, ingredients of culture media, buffers such as a phosphate buffer and HEPES buffer, and/or adjuvants such as cytokines and CpG oligodeoxynucleotide. As long as not pharmacologically detrimental, the vaccine may contain any ingredients such as preservatives. In addition, the vaccine of the present invention can be used in a mixture with any recombinant or non-recombinant viruses such as the MDV serotype 1 or serotype 2 vaccine strains.

Any known method is applicable to the preparation of the recombinant bivalent vaccine in the present invention. For instance, the recombinant HVT may be inoculated into permissive culture cells such as CEF cells and grown to an appropriate titer. Then, the cells are removed from tissue culture plates or roller bottles with cell scrapers or by trypsin treatment and collected by centrifugation. The pelleted cells are then suspended in culture medium containing dimethyl sulfoxide, frozen slowly, and then stored in liquid nitrogen. Alternatively, the recombinant HVT may be released from the infected cells by disrupting the cells in diluents containing stabilizers such as sucrose and bovine albumin. These released HVT is called cell-free HVT. Cell-free HVT may be lyophilized and stored at 4° C.

The bivalent recombinant HVT vaccine can be administered to chickens by any known method of inoculating Marek's disease vaccine. For instance, the vaccine of the present invention is diluted to give $10^1$-$10^5$, or more favorably $10^2$-$10^4$ plaque forming units (pfu) per dose with a diluent containing buffer components, sugars, and dye. The diluted vaccine may be inoculated subcutaneously behind the neck of one-day-old chicks or into embryonating eggs via the in ovo route with syringes or with any apparatus for injection.

The present avian bivalent vaccine is able to confer serological titer by HI of more than 50 (geometric mean titer) in groups of vaccinated chickens by 5 weeks post inoculation, when using four hemagglutination units of an inactivated avian influenza virus homologous H5 subtype antigen for the HI tests. Also the bivalent vaccine in the present invention provided excellent protection against lethal challenge with highly pathogenic avian influenza virus (H5N1).

BRIEF DESCRIPTION OF THE DRAWINGS

FIG. 6 Western blot assay detecting expression of the hemagglutinin protein by the recombinant turkey herpesvirus.

FIG. 7 Hemagglutination inhibition titers in chickens vaccinated with the recombinant turkey herpesvirus with hemagglutinin gene.

FIG. 8 ELISA titers in chickens vaccinated with the recombinant turkey herpesvirus with hemagglutinin gene using a commercial ELISA kit (IDEXX LABORATORIES, FLOCKCHEK AIV).

FIG. 9 ELISA titers in chickens vaccinated with the recombinant turkey herpesvirus with hemagglutinin gene using a commercial ELISA kit (SYNBIOTICS, PROFLOK AIV Ab test kit).

FIG. 10 Hemagglutination inhibition titers in chickens vaccinated with the recombinant turkey herpesvirus with hemagglutinin gene (second trial).

DETAILED DESCRIPTION OF THE INVENTION

Figure 1:
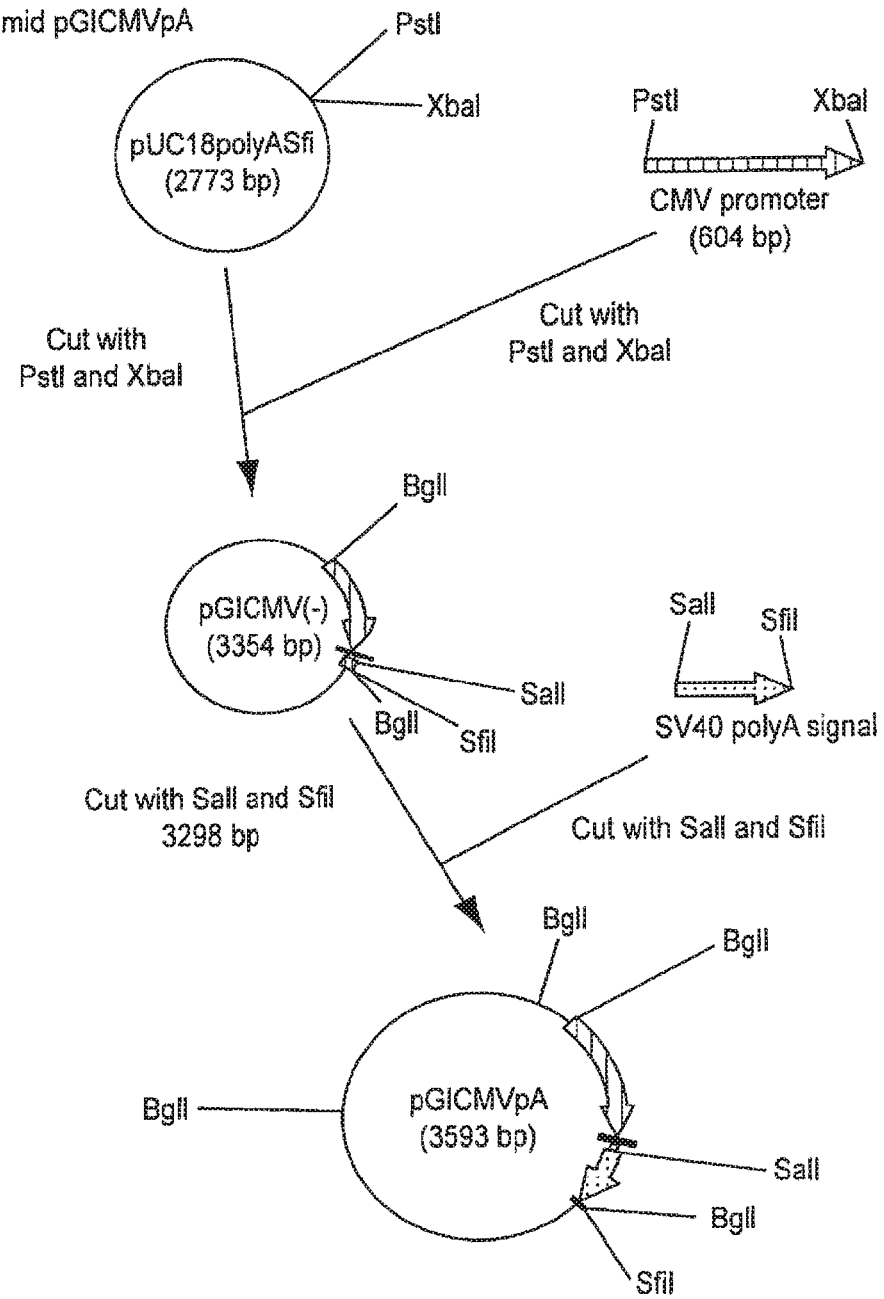
FIG. 1 Construction of the plasmid pGICMVpA.

Gene cloning and plasmid construction was essentially performed by the standard molecular biology techniques (Molecular Cloning: A Laboratory Manual. 3rd Edition, Cold Spring Harbor Laboratory Press, Woodbury, N.Y. 2001). The turkey herpesvirus FC126 strain (R. L. Witter et al., 1970, Am. J. Vet. Res. 31, 525-538) was used as a backbone virus to generate a recombinant turkey herpesvirus.

EXAMPLE 1

Hemagglutinin Gene Isolation from Avian Influenza Virus H5 Subtype

The avian influenza virus A/Turkey/Wisconsin/68 (H5N9) strain was propagated in the allantoic sac of specific pathogen free embryonating chicken eggs. Total genomic RNA from the A/Turkey/Wisconsin/68 virus was extracted using RNEASY MINI KIT (QIAGEN, Cat #74104). First-strand cDNA was synthesized with SUPERSCRIPT FIRST-STRAND System for RT-PCR (Invitrogen, Cat #11904-018). Using the resulting cDNA as a template, the HA gene was amplified by polymerase chain reaction (PCR) with PFUULTRA HIGH FIDELITY DNA Polymerase (STRATAGENE, Cat #600380) and PCR primers. These PCR primers, BamHA-F primer (SEQ ID NO: 4) and SalHA-R primer (SEQ ID NO: 5), anneal to the start and stop sequences of the HA gene and each primer contains a sequence at the 5' ends for a restriction enzyme, BamHI or SalI, respectively. After the PCR reaction, Taq polymerase (PROMEGA, Cat # M2665) was added to the PCR mixture to add 3' A-overhangs to the PCR products.

```
BamHA-F primer
                                      (SEQ ID NO: 4)
5'-TGACGGATCCATGGAAAGAATAGTGATTG-3'

SalHA-R primer
                                      (SEQ ID NO: 5)
5'-CTGACAGTCGACCTAGATGCAAATTCTGC-3'
```

The amplified 1.8 kilobase (kb) HA cDNA was inserted into PCR2.1-TOPO vector (INVITROGEN, Cat # K4500-01), resulting in pCR2.1-H5Wis68. Nucleotide sequences of the HA genes in a few clones of the plasmid pCR2.1-H5Wis68 and the PCR product were determined using ABI PRISM 3730XL DNA Analyzer (APPLIED BIOSYSTEMS) with six primers; BamHA-F primer (SEQ ID NO: 4), SalHA-R primer (SEQ ID NO: 5), M13 Forward primer (SEQ ID NO: 6), M13 Reverse primer (SEQ ID NO: 7), HA-F primer (SEQ ID NO: 8), and HA-R primer (SEQ ID NO: 9).

```
M13 Forward primer
                                      (SEQ ID NO: 6)
5'-GTAAAACGACGGCCAGT-3'

M13 Reverse primer
                                      (SEQ ID NO: 7)
5'-GGAAACAGCTATGACCATG-3'

HA-F primer
                                      (SEQ ID NO: 8)
5'-CTGGACAATACTAAGGCCGAACGAT-3'

HA-R primer
                                      (SEQ ID NO: 9)
5'-CACTGGGGTCTGACATTTGGTA-3'
```

The sequences in the clones of the plasmid pCR2.1-H5Wis68 were identical to each other and to the sequence of the PCR product. Although the deduced amino acid sequence was different from the reported sequence of A/Turkey/Wisconsin/68 (H5N9) (M. Garcia et al., 1997, Virus Res. 51: 115-124, GenBank Accession # U79456) by four amino acids, the amino acids we obtained were the same as the amino acids of a majority of H5 subtype HA proteins. The nucleotide sequence and the deduced amino acid sequence of the HA gene obtained from A/Turkey/Wisconsin/68 (H5N9) are shown in SEQ ID NO: 1 and SEQ ID NO: 2.

EXAMPLE 2

Construction of Homology Plasmids 2-1. A Summary of Homology Plasmids and Recombinant Turkey Herpesviruses In the present invention, three promoters, the CMV promoter, the chicken beta-actin promoter (Bac promoter), and a modified chicken beta-actin promoter (Pec promoter), were used to control expression of the HA gene of the AI virus A/Turkey/Wisconsin/68 (H5N9) strain. First, homology plasmids with the HA gene and one of the promoters were constructed and then recombinant turkey herpesviruses were generated using the homology plasmids. The recombinant turkey herpesviruses with different promoters were compared for capabilities of conferring serological titers against AI in chickens as shown in EXAMPLE 6. A recombinant HVT with the CMV promoter is presented here as an example and recombinant viruses with the Bac promoter or the Pec promoter are presented here as comparative examples. A list of the homology plasmids and the recombinant turkey herpesviruses constructed in the present invention is shown in TABLE 1.

TABLE 1

A list of homology plasmids and recombinant turkey herpes viruses

| Item # | Name of homology plasmids | Name of recombinant viruses | Promoters | Examples vs. comparative examples |
|---|---|---|---|---|
| 1 | p45CMVH5Wis68 | rHVT/CMVH5Wis68 | CMV promoter | Example |
| 2 | p45BacH5Wis68 | rHVT/BacH5Wis68 | Bac promoter | Comparative example |
| 3 | p45PecH5Wis68 | rHVT/PecH5Wis68 | Pec promoter | Comparative example |

2-2. Construction of Plasmid pGICMVpA

The CMV promoter was obtained from pBK-CMV (STRATAGENE, Cat. #212209). Three BglI restriction enzyme sites in the CMV promoter were disrupted for ease of the plasmid construction process by PCR in vitro mutagenesis using four pairs of primers. The primer pairs were PrCMV1 (SEQ ID NO: 10) and PrCMV3 (SEQ ID NO: 12), PrCMV4 (SEQ ID NO: 13) and PrCMV5 (SEQ ID NO: 14), PrCMV6 (SEQ ID NO: 15) and PrCMV2' (SEQ ID NO: 11), and PrCMVo1 (SEQ ID NO: 16) and PrCMVR1 (SEQ ID NO: 17). Four PCR reactions were conducted separately using each pair of primers and pBK-CMV as a template. Then four PCR products were combined and used as a template for the secondary PCR with primers PrCMV1 and PrCMVR1, yielding the 604 bp fragment with a modified CMV promoter sequence. The nucleotide sequence of the CMV promoter used to express HA gene is provided in SEQ ID. NO. 3. The CMV promoter fragment was digested with PstI and XbaI and inserted into PstI and XbaI digested pUC18polyASfi (U.S. Pat. No. 6,866,852), resulting in pGICMV(−). The SV40 polyA signal was obtained from pBK-CMV by PCR using primers PolyA-SalKpn (SEQ ID NO: 18) and PolyA-SfiF2 (SEQ ID NO: 19). The PCR fragment containing SV40 polyA signal was digested with SalI and SfiI and ligated to pGICMV(−) digested with SalI and SfiI resulting in pGICMVpA (FIG. 1).

PrCMV1
(SEQ ID NO: 10)
5'-GGGCTGCAGAGTTATTAATAGTAATCAATT-3'

PrCMV2'
(SEQ ID NO: 11)
5'-CGCGCCATTTACCGTCATTGACGTC-3'

PrCMV3
(SEQ ID NO: 12)
5'-GGGTCGTTGGGCGGTCAGCCGGCGG-3'

PrCMV4
(SEQ ID NO: 13)
5'-CTTACGGTAAATGGCCCGCCGGCTG-3'

PrCMV5
(SEQ ID NO: 14)
5'-TACACTTGATGTACTGCCAATGGGC-3'

PrCMV6
(SEQ ID NO: 15)
5'-TATTTACGGTAAACTGCCCATTGGC-3'

PrCMVo1
(SEQ ID NO: 16)
5'-ACGTCAATGACGGTAAATGGCGCGCCTGGC-3'

PrCMVR1
(SEQ ID NO: 17)
5'-CGTCTAGAGGATCTGACGGTTCACTAAACC-3'

PolyA-SalKpn
(SEQ ID NO: 18)
5'-TGTGGTACCGTCGACGATTCACAGTCCCAAGGC-3'

PolyA-SfiF2
(SEQ ID NO: 19)
5'-CTTGGCCTTATTGGCCTAAGATACATTGATGAG-3'

2-3. Construction of Homology Plasmid p45CMVH5Wis68

Figure 2:
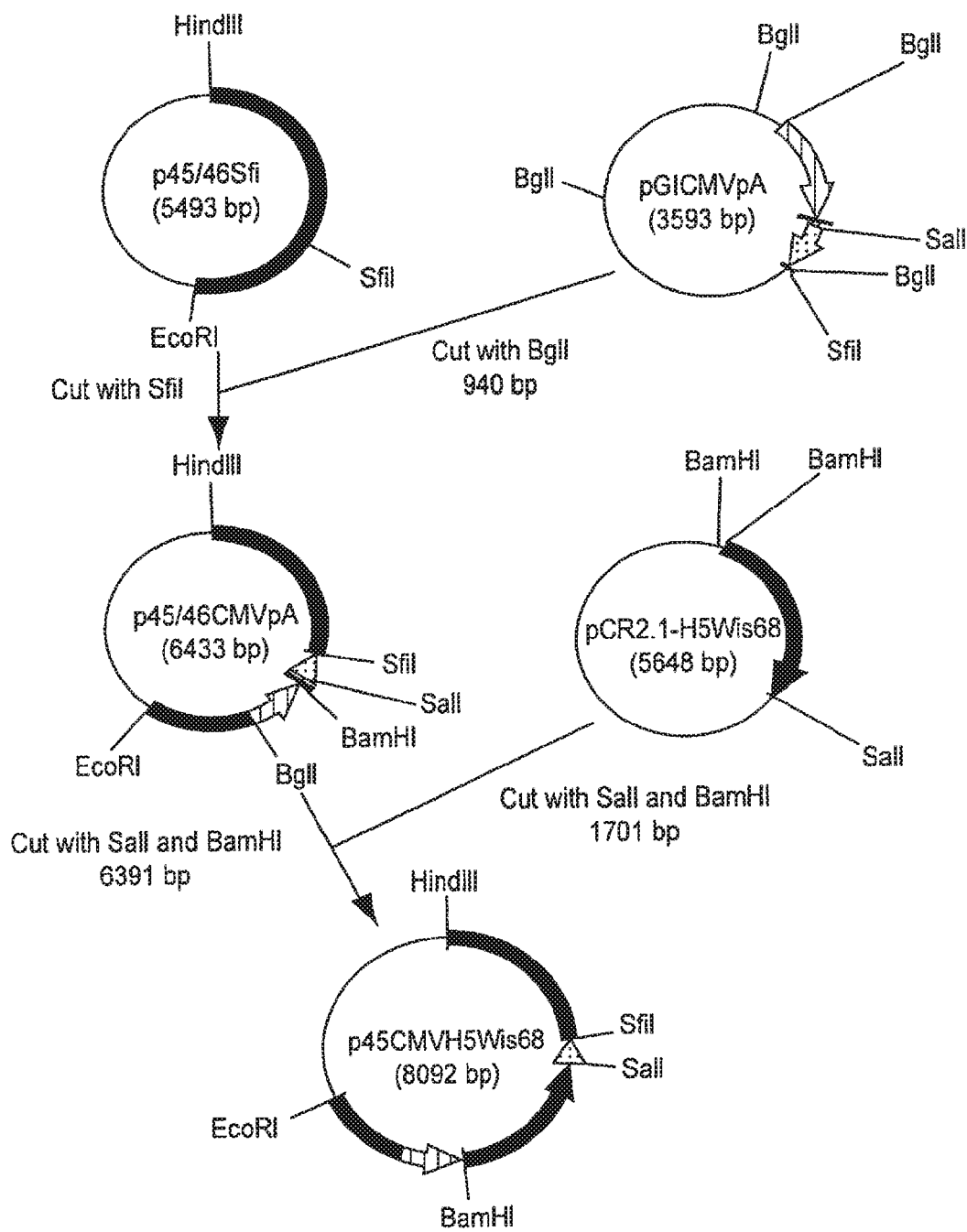
FIG. 2 Construction of the homology plasmid p45CMVH5Wis68.

The CMV promoter and the SV40 polyA signal (940 bp) were excised from pGICMVpA by BglI and ligated into SfiI digested p45/46Sfi (U.S. Pat. No. 6,866,852), resulting in p45/46CMVpA. Then, the HA gene from A/Turkey/Wisconsin/68 (H5N9) was excised from pCR2.1-H5Wis68 using SalI and BamHI. The 1701 bp HA gene was inserted into p45/46CMVpA digested with SalI and BamHI, resulting in p45CMVH5Wis68 (FIG. 2). The plasmid p45CMVH5Wis68 was used as a homology plasmid to generate recombinant turkey herpesvirus.

2-4. Construction of Plasmid pGIBacpA2nd

Figure 3:
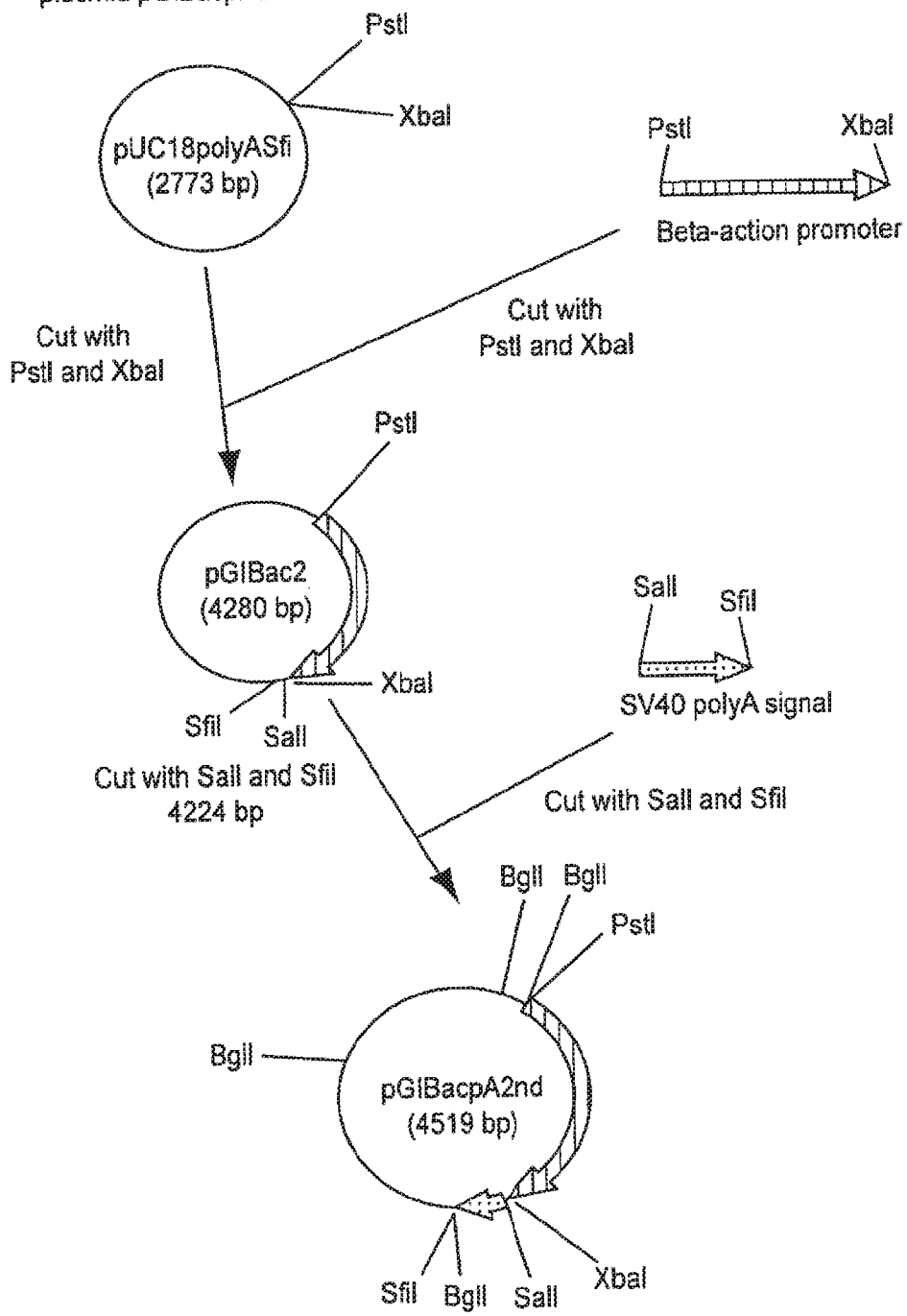
FIG. 3 Construction of the plasmid pGIBacpA2nd.

The Bac promoter was obtained by PCR using cellular DNA of CEF cells as a template. PrBac1 (SEQ ID NO: 18) and PrBac2' (SEQ ID NO: 19) were the primer set used for PCR. An obtained 1.5-kilobase DNA fragment was digested with PstI and XbaI and inserted into PstI and XbaI digested pUC18polyASfi, resulting in pGIBac2. Then, the SV40 polyA signal obtained PCR using primers PolyA-SalKpn (SEQ ID NO: 18) and PolyA-SfiF2 (SEQ ID NO: 19) was digested with SalI and SfiI and ligated to pGIBac2 digested with SalI and SfiI resulting in pGIBacpA2nd (FIG. 3).

PrBac1
(SEQ ID NO: 20)
5'-CAGTGTCGCTGCAGCTCAGTGCATGCACGCTCATTGCCC-3'

PrBac2'
(SEQ ID NO: 21)
5'-GCTCTAGAGGCGTGGAGCTTGGGGGCTGCGGAGGAACAGAGAAGGGAAG-3'

2-5. Construction of Homology Plasmid p45BacH5Wis68

Figure 4:
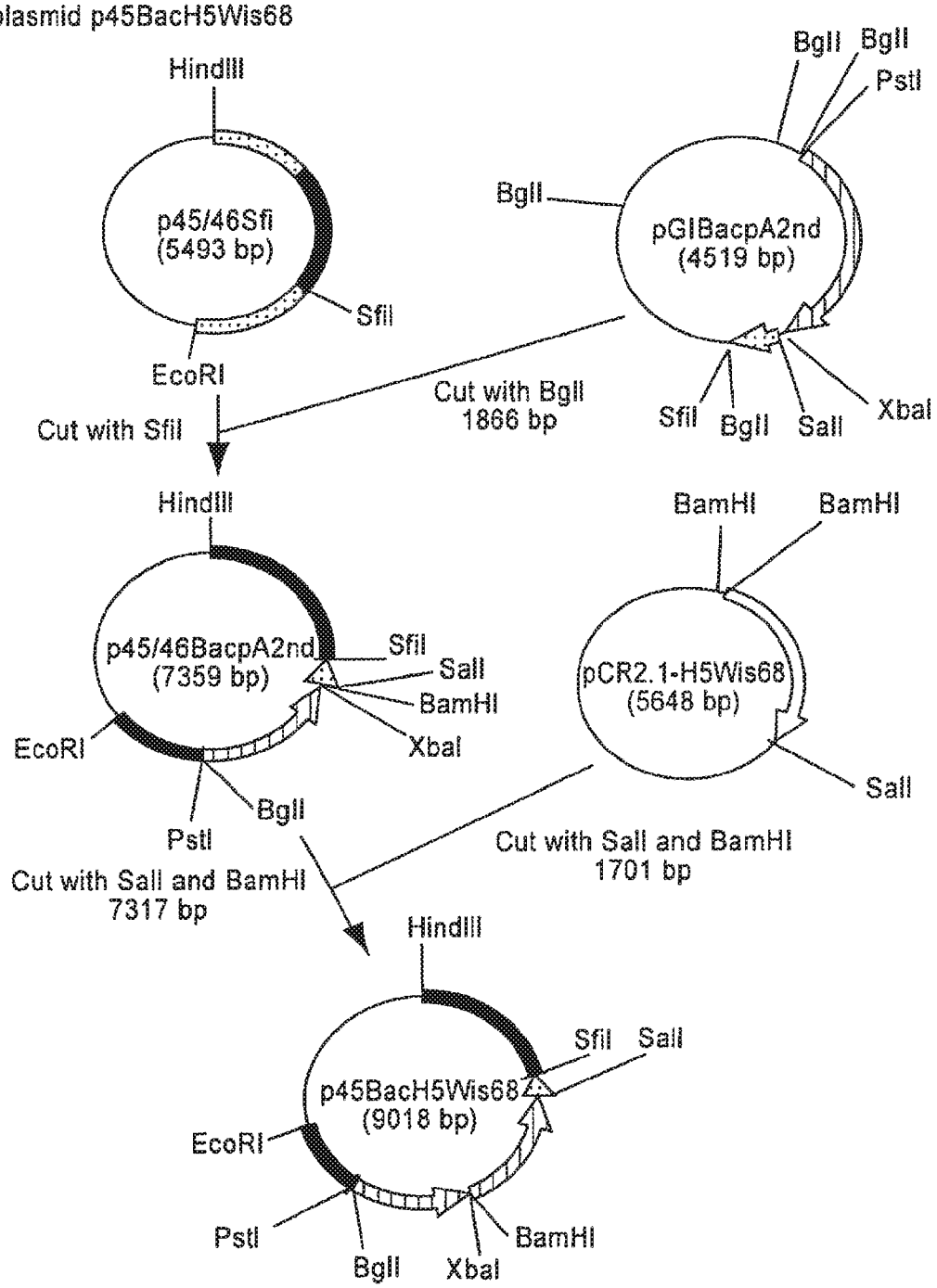
FIG. 4 Construction of the homology plasmid p45BacH5Wis68.

The Bac promoter and the SV40 polyA signal (1866 bp) were excised from pGIBacpA2nd by BglI and ligated into SfiI digested p45/46Sfi, resulting in p45/46BacpA2nd. Then, the HA gene of A/Turkey/Wisconsin/68 (H5N9) excised from pCR2.1-H5Wis68 using SalI and BamHI was inserted into p45/46BacpA2nd digested with SalI and BamHI, resulting in p45BacH5Wis68 (FIG. 4).

2-6. Construction of Homology Plasmid p45PecH5Wis68

Figure 5:
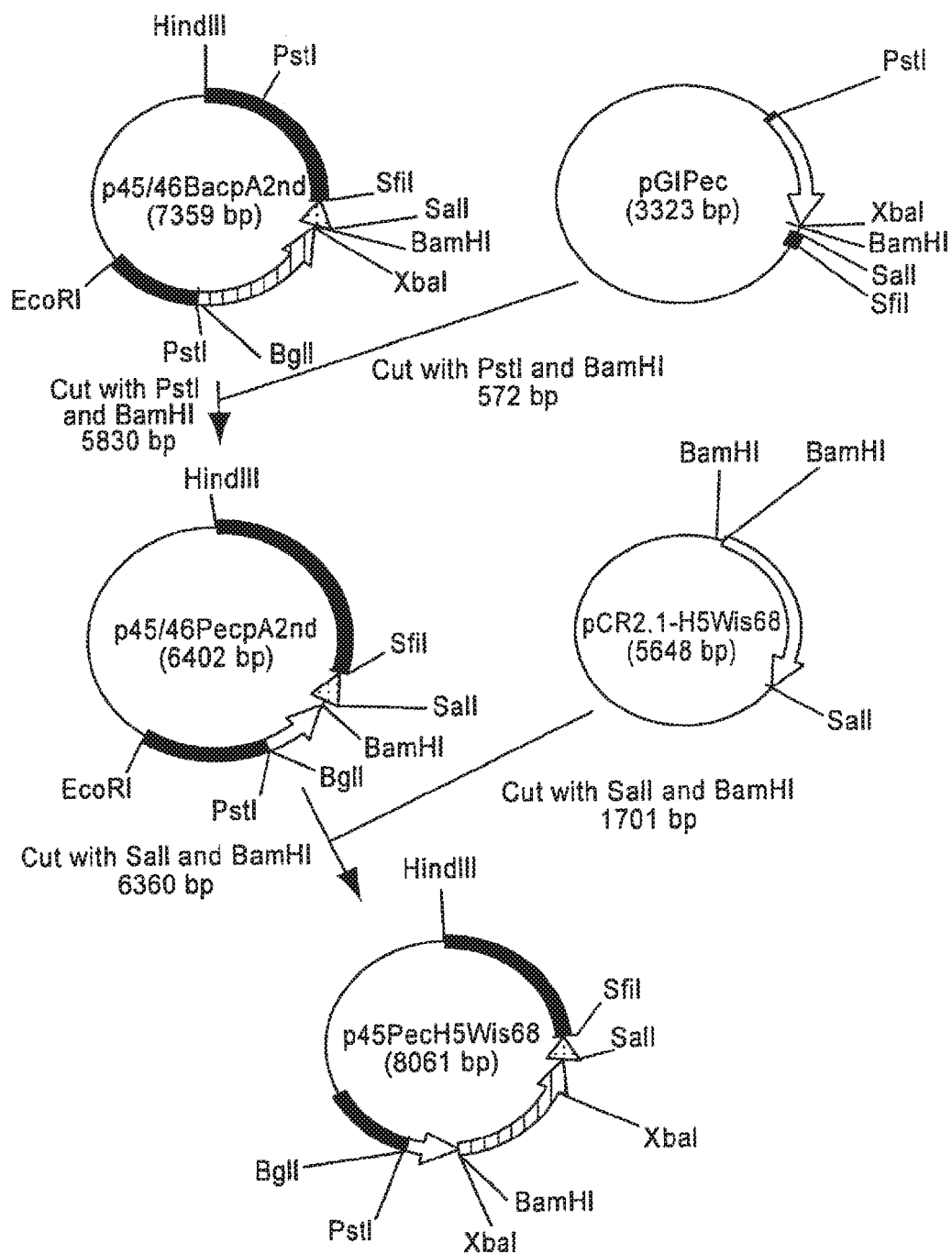
FIG. 5 Construction of the homology plasmid p45PecH5Wis68.

Construction of the Pec promoter is described in U.S. Pat. No. 6,866,852. The Pec promoter was synthesized by fusing a part of the chicken beta-actin promoter with the enhancer region of the CMV promoter. The Pec promoter was excise from pGIPec (U.S. Pat. No. 6,866,852) with PstI and BamHI and inserted into PstI and BamHI digested p45/46BacpA2nd described in EXAMPLE 2-4, resulting in p45/46PecpA2nd. Then, the HA gene of A/Turkey/Wisconsin/68 (H5N9) excised from pCR2.1-H5Wis68 using SalI and BamHI was inserted into p45/46PecpA2nd digested with SalI and BamHI, resulting in p45PecH5Wis68 (FIG. 5).

EXAMPLE 3

Generation and Isolation of Recombinant Turkey Herpesvirus

Viral DNA of the HVT FC126 strain was prepared as described by Morgan et al. (Avian Diseases, 1990, 34:345-351).

$10^7$ secondary chicken embryo fibroblast (CEF) cells were suspended in Saline G (0.14 M NaCl, 0.5 mM KCl, 1.1 mM $Na_2HPO_4$, 1.5 mM $NaH_2PO_4$, 0.5 mM $MgCl_2$, and 0.011% glucose) and co-transfected with HVT viral DNA and 5 to 25 µg of the homology plasmid, p45CMVH5Wis68, p45BacH5Wis68, or p45PecH5Wis68 by electroporation. Electroporation was performed using BIO-RAD GENE PULSER. Transfected cells were incubated for 10 minutes at room temperature and transferred to wells of 96-well plates. After incubating at 37° C. for 7 days in 4-5% $CO_2$, or until the plaques became visible, the cells were detached from the plates by trypsinization, transferred equally to two 96-well plates with secondary CEF and incubated for 3 to 4 days until plaques were observed. Screening was conducted by the black plaque assay, staining only plaques expressing HA protein. Briefly, one of the two plates was fixed with methanol:acetone mixture (1:2) and incubated with chicken anti-HA antiserum. Next, incubated with biotinylated anti-chicken IgG antibody (VECTOR LABORATORIES, Cat # BA-9010) and then with VECTASTAIN ABC-AP kit (Vector Laboratories, Cat # AK-5000), plaques expressing HA protein were stained by addition of BCIP/NBT solution (BIO-RAD LABORATORIES, Cat #170-6539 and 170-6532). Wells containing stained recombinant plaques were identified and cells from the corresponding wells on the other 96-well plate were trypsinized. The cells were then diluted in fresh secondary CEF cells and transferred to 96-well plates to complete the first round of purification.

The purification procedure was repeated until all plaques were stained positively in the black plaque assay. Purified recombinant virus with the HA gene under the CMV promoter was designated as rHVT/CMVH5Wis68 (the present invention). Recombinant viruses with the Bac promoter or the Pec promoter were designated as rHVT/BacH5Wis68 and rHVT/PecH5Wis68, respectively (comparative examples).

EXAMPLE 4

Verification of Genome Structure and Stability of Recombinant HVT 4-1. Southern Blot Analysis Chicken embryo fibroblast cells in a 100-mm dish that were infected with the recombinant virus, rHVT/CMVH5Wis68 or the HVT FC126 parent strain were used in the Southern blot analysis to confirm the insertion of the HA gene in the desired insertion site. The cells were collected by a cell scraper and by centrifugation at 913×g for 5 minutes. The harvested cells were washed with phosphate buffered saline (PBS) and resuspended in 1.0 milliliter (ml) of lysis buffer (0.5% TRITON X-100, 100 mM 2-mercaptethanol, and 20 mM EDTA in PBS). The cell suspension was vortexed for a total of 30 seconds and incubated for 15 minutes at room temperature. Cell nucleus and cell debris were removed by centrifuging at 2,060×g for 5 minutes and the supernatant was transferred to a 1.5-ml tube. Viruses were collected by centrifugation at 20,800×g for 20 minutes at 4° C. The pellet was suspended in 0.33 ml of a nuclease solution (12.5 mM Tris-Cl (pH7.5), 1 μg/ml DNase I and 1 μg/ml RNase A) and incubated at 37° C. for 30 minutes. Then, 83 μl of SDS-protease solution (50 mM EDTA, 5% SDS, 0.5 mg/ml protease K, and 25 mM 2-mercaptoethanol) was added to the virus suspension and incubated at 55° C. for 30 minutes to disrupt virus envelopes. Phenol chloroform extraction was conducted twice and DNA was precipitated by adding 2.5 volume of cold 100% ethanol and NaCl at a final concentration of 0.16 M. After centrifuging at 20,800×g for 30 minutes at 4° C., the pellet was washed with 70% ethanol and air-dried. The pellet was dissolved in TE buffer (10 mM Tris-Cl (pH8.0), and 1 mM EDTA).

The viral DNA in TE buffer and the homology plasmid (positive control) were digested with XhoI, BamHI and SpeI and separated by agarose gel electrophoresis using 0.6% agarose gel. DNA fragments on the gel were transferred to a BIODYNE A nylon membrane (PALL, Cat # BNXF3R). The membrane was hybridized with either Digoxigenin (DIG)-labeled HA probe or DIG-labeled IS45/46 probe. The DIG-labeled HA probe and the IS45/46 probe were prepared with PCR DIG Probe Synthesis Kit (ROCHE APPLIED SCIENCE, Cat #11636090910) using primers HA1-P-F (SEQ ID NO: 22) and HA1-P-R (SEQ ID NO: 23) and primers 45/46-F (SEQ ID NO: 24) and 45/46-R (SEQ ID NO: 25), respectively.

```
HA1-P-F
                                    (SEQ ID NO: 22)
5'-GGGGGTGGCAAGGAATG-3'

HA1-P-R
                                    (SEQ ID NO: 23)
5'-GCTAGGGAACTCGCCACTGT-3'

45/46-F-B
                                    (SEQ ID NO: 24)
5'-TAGCGGCACGGAAACAGATAGAGA-3'

45/46-R-B
                                    (SEQ ID NO: 25)
5'-TGGCGATACGGTTCCTGGTTTGAC-3'
```

The membrane was washed with 2×SSC solution at room temperature and then with 0.5×SSC solution at 68° C. The membrane was blocked and incubated with anti-Digoxigenin-AP, Fab fragments (ROCHE APPLIED SCIENCE, Cat #11093274910) for 30 minutes at room temperature. After washing two times with maleic acid washing buffer (0.1 M maleic acid, 0.15 M NaCl, and 0.3% Tween20, pH 7.5), DNA bands that were hybridized with the probes were visualized by incubating the membrane with BCIP/NBT solution. The HA probe hybridized with 3.6 kb bands in the recombinant virus DNA and the homology plasmid, while no bands were detected with the HVT parent. The IS45/46 probe hybridized with 3.6 kb and 1.2 kb bands in the recombinant DNA and the homology plasmid, and with 2.3 kb band in the HVT parent. These results demonstrated that rHVT/CMVH5Wis68 obtained in EXAMPLE 3 had an expected genomic structure.

Southern blot analysis of rHVT/BacH5Wis68 and rHVT/PecH5Wis68 was conducted in a similar way as that of rHVT/CMVH5Wis68, except that XhoI and SpeI restriction enzymes were used for rHVT/BacH5Wis68. For rHVT/BacH5Wis68, the HA probe hybridized with 4.9 kb bands in the recombinant virus DNA and the homology plasmid, while no bands were detected with the HVT parent. The IS45/46 probe hybridized with 4.9 kb and 0.8 kb bands in the recombinant DNA and the homology plasmid, and with 2.3 kb band in the HVT parent. For rHVT/PecH5Wis68, the HA probe hybridized with 3.6 kb bands in the recombinant virus DNA and the homology plasmid, while no bands were detected with the HVT parent. The IS45/46 probe hybridized with 3.6 kb and 1.2 kb bands in the recombinant DNA and the homology plasmid, and with 2.3 kb band in the HVT parent. These recombinant viruses were also demonstrated to have expected genomic structures.

4.2. Stability of Recombinant HVT

The recombinant viruses, rHVT/CMVH5Wis68, rHVT/BacH5Wis68, and rHVT/PecH5Wis68, were passed 20 times blindly in CEF cells. After the 20 passages, the viruses were analyzed by the Southern blot analysis as described in EXAMPLE 4.1. Bands detected in DNA isolated from the virus after 20 passages were identical to the bands described in EXAMPLE 4.1, demonstrating that the recombinant viruses were stable even after 20 passages.

EXAMPLE 5

HA Protein Expression by Recombinant HVT

Expression of the HA protein by the recombinant viruses, rHVT/CMVH5Wis68, rHVT/BacH5Wis68, and rHVT/PecH5Wis68, was confirmed by the black plaque assay and the Western blot assay. Procedures for the black plaque assay are described in EXAMPLE 3. The western blot was conducted using CEF cells infected with the recombinant viruses and chicken anti-HA antiserum. Briefly, CEF cells in 100-mm dishes were infected with one of the recombinant viruses or the parent HVT FC126 strain at a multiplicity of infection of approximately 0.01. Two to three days post inoculation, cells were harvested with cell scrapers and centrifuged at 913×g for 5 minutes. The pellet was washed with PBS twice and resuspended with 50 to 100 μl of PBS. After adding the same volume of 2×SDS sample buffer (130 mM Tris-Cl (pH6.8), 6% SDS, 20% Glycerol, 10% 2-Mercaptoethanol and 0.01% Bromo Phenol Blue), cell suspension was boiled for 5 minutes. The samples were separated by SDS-PAGE using 8% polyacrylamide gel and transferred to a PVDF membrane (IMMOBILON-P, MILLIPORE). The membrane was dried completely and then incubated with chicken anti-HA antiserum. After the anti-HA antiserum was washed off, the membrane was incubated with alkaline phosphatase-conjugated anti-chicken IgG Fc antibody (BETHYL, Cat # A30-104AP). Protein bound with chicken anti-HA antiserum was visualized by adding BCIP/NBT solution. As shown in FIG. 3, a protein band of 74 kilodaltons (kDa) was observed only in the lane with the recombinant virus infected cells, which was the expected size of the non-processed HA protein.

EXAMPLE 6

Serological Evaluation of Chickens Inoculated with Recombinant HVT

Serological responses against AI in chickens that were vaccinated with the recombinant viruses, rHVT/CMVH5Wis68, rHVT/PecH5Wis68, and rHVT/BacH5Wis68, were evaluated. One-day-old specific pathogen free chicks (SPAFAS, Flock T-10) were vaccinated subcutaneously with one of the recombinant viruses. Groups 1 and 2 were inoculated with 1638 pfu per dose (0.2 ml) and 375 pfu per dose of rHVT/CMVH5Wis68, respectively (TABLE 2). Groups 3 and 4 contained chickens vaccinated with 2800 pfu (Group 3) or 550 pfu (Group 4) of rHVT/PecH5Wis68. Groups 5 and 6 were inoculated with 4350 pfu and 720 pfu per dose of rHVT/BacH5Wis68, respectively. A group of chickens (Group 8) were held as non-inoculated negative controls. Another group of chickens (Group 7) was vaccinated subcutaneously with inactivated A/Turkey/Wisconsin/68 (H5N9) vaccine at three weeks old as an inactivated vaccine control. Chickens were bled between 3 to 7 weeks old and obtained sera were evaluated by the AI HI tests and AIV ELISA tests. The AI HI tests were conducted using four hemagglutination units of an inactivated avian influenza virus homologous antigen of the A/Turkey/Wisconsin/68 (H5N9) strain, the HA gene of which was used in the recombinant viruses, as described by D. E. Swayne et al (D. E. Swayne et al., 1998, Avian Influenza. In: A Laboratory Manual for the Isolation and Identification of Avian Pathogens, 150-155). Briefly, before the HI assay, the number of the hemagglutination units in the inactivated A/Turkey/Wisconsin/68 (H5N9) antigen was determined as the highest dilution of the antigen giving complete agglutination, and the antigen was diluted to contain four hemagglutination units in 25 μl. In U-bottom 96 well plates, the sera were initially diluted 1:5 and then serially diluted by two fold across the plates with phosphate buffered saline (PBS) to contain 25 μl per well. Four hemagglutination units of the antigen in 25 μl were added to each well and incubated for 30 minutes at room temperature. Finally, 50 μl of 0.5% chicken erythrocytes in PBS was added to each well and incubated for about 40 minutes at room temperature. HI titers are the highest dilution of the sera exhibiting inhibition of hemagglutination. HI titers of equal to or more than 10 were considered positive. The ELISA tests were conducted using two commercial AIV ELISA kits (IDEXX Laboratories, FLOCKCHEK AIV and SYNBIOTICS, PROFLOK AIV Ab test kit) that are available in the United States.

As shown in TABLE 3 and FIG. 7, sera from chickens vaccinated with rHVT/CMVH5Wis68 (Groups 1 and 2) started to show HI titers as early as three weeks post vaccination and the HI titers continued to increase up to the HI titer of 100 (geometric mean titer) by six weeks post vaccination. Also, more than 80% of vaccinated chickens at three weeks post vaccination and all vaccinated chickens after five weeks post vaccination had HI titers of equal to or more than 10 (TABLE 3). High levels of HI titers have not been consistently observed with the commercial fowlpox-vectored AIV vaccine and this was not easily accomplished. The dose difference between two vaccine groups (1638 pfu and 375 pfu) did not have a significant influence on serological responses. Surprisingly, when tested with the commercial AIV ELISA kits, these sera from rHVT/CMVH5Wis68-vaccinated chickens that were highly positive by the HI tests did not give positive ELISA titers through 3 and 7 weeks post vaccination, whereas sera collected from the inactivated vaccine control (Group 7) showed highly positive ELISA titers with both commercial ELISA kits (FIGS. 8 and 9). This feature of the rHVT/CMVH5Wis68 vaccine would make it extremely easy to differentiate vaccine reactions from field virus exposure and to track vaccinated chickens. Geometric mean HI titers of sera from chickens vaccinated with rHVT/PecH5Wis68 (Groups 3 and 4) or rHVT/BacH5wis68 (Groups 5 and 6) were not as high as those conferred by rHVT/CMVH5Wis68. Also, rHVT/PecH5Wis68 and rHVT/BacH5wis68 failed to confer serological titer by HI to vaccinated chickens consistently as shown in TABLE 3. The non-inoculated negative controls (Group 8) did not show positive serological results in either the HI tests or the ELISA tests throughout the observation period.

In summary, the recombinant HVT with the HA gene in combination with the CMV promoter (rHVT/CMVH5wis68) provided vaccinated chickens with higher and more uniform serology titers by HI than the recombinant HVT with the Bac promoter (rHVT/BacH5Wis68) and the recombinant HVT with the Pec promoter (rHVT/PecH5Wis68), which are presented here as comparative examples. The sera collected from chickens vaccinated from rHVT/CMVH5Wis68 were negative by commercially available AIV ELISA kits although the sera were highly positive by the AI HI tests, thus enabling easy differentiation between reaction from vaccination and field infection.

EXAMPLE 7

Second Serological Evaluation of Chickens Inoculated with Recombinant HVT

In order to further investigate the potency of the recombinant HVT with the HA gene, another serological evaluation test was conducted. Specific pathogen free chickens (SPAFAS, Flock R105) were divided into four groups in this study (TABLE 4). Embryos at 18 days of incubation in Group 1 was vaccinated with 980 pfu per dose (0.1 ml) of rHVT/CMVH5Wis68 via the in ovo route. Group 2 and Group 3 were vaccinated subcutaneously at one day old with 695 pfu per dose (0.2 ml) of rHVT/CMVH5Wis68 or 1155 pfu per dose of rHVT/BacH5Wis68, respectively. A group of chickens (Group 4) were held as non-inoculated negative controls. Chickens were bled between 2 to 7 weeks old and obtained sera were evaluated by the AI HI tests and AIV ELISA tests. The AI HI tests were conducted using four HA units of an inactivated A/Turkey/Wisconsin/68 (H5N9) antigen as described by D. E. Swayne et al (D. E. Swayne et al., 1998, Avian Influenza. In: A Laboratory Manual for the Isolation and Identification of Avian Pathogens, 150-155).

As shown in TABLE 5 and FIG. 10, rHVT/CMVH5Wis68 by subcutaneous administration (Group 2) again showed excellent potency as in the first trial. HI titers in this group reached 100 (geometric mean titer) by three weeks post vaccination and high levels of HI titers were maintained through seven weeks post vaccination. Also, in this study, we found that in ovo administration of rHVT/CMVH5Wis68 (Group 1) is as potent as subcutaneous administration. HI titers in Group 1 were very similar to those in Group 2. Titers from chickens vaccinated with rHVT/BacH5Wis68 (Group 3) were somewhat lower than those from chickens vaccinated with rHVT/CMVH5Wis68 (Groups 1 and 2) again except at 5 weeks post vaccination when Group 3 had a higher HI titers than other groups, but the HI titer dropped at following weeks. No detectable HI titers were observed from non-inoculated negative controls throughout the observation period.

EXAMPLE 8

Efficacy of Recombinant HVT Against Highly Pathogenic Avian Influenza Virus (H5N1) Challenge In the third trial, the efficacy of the recombinant HVT with the HA gene against highly pathogenic avian influenza virus (H5N1 subtype) was examined. Specific pathogen free chickens were divided into four groups in this study (TABLE 6). One-day-old chicks in Groups 1 and 2 were vaccinated with 1075 pfu per dose (0.2 ml) of rHVT/CMVH5Wis68 and 1080 pfu per dose of rHVT/BacH5Wis68, respectively. Chicks in Group 3 (unvaccinated, challenged positive control) were inoculated with vaccine diluent and challenged at four weeks old. Group 4 was held as non-vaccinated, non-challenged negative controls.

At four weeks old, chickens in Groups 1, 2 and 3 were challenged intranasally with $10^{5.0}$ $EID_{50}$ (200 $LD_{50}$) of highly pathogenic avian influenza virus A/Viet Nam/1203/04 (H5N1) strain. Protection was evaluated by mortality and clinical signs of avian influenza. All chickens in Group 3 (unvaccinated, challenged positive control) died within two days after challenge, confirming severity of the challenge (Table 7). rHVT/CMVH5Wis68 showed excellent protection against lethal highly pathogenic avian influenza challenge, as in Group 1, vaccinated with rHVT/CMVH5Wis68, 95% (19 out of 20 chickens) were protected. On the other hand, only 65% (13 out of 20) of chickens in Group 2 (rHVT/BacH5Wis68) survived the challenge. All chickens in Group 4 (non-vaccinated, non-challenged negative control) were free from mortality and clinical signs of avian influenza. As is consistent with two serological evaluation studies described in EXAMPLE 6 and 7, the recombinant HVT with the HA gene in combination with the CMV promoter (rHVT/CMVH5wis68) provided much better protection against challenge with highly pathogenic avian influenza virus (H5N1) than the recombinant HVT with the Bac promoter (rHVT/BacH5Wis68), which is presented here as a comparative example.

TABLE 2

Treatment groups

| Group # | Treatment Group | Promoters | Age of vaccination | Vaccine dose (pfu[1]) | Vaccine route | # of chickens |
|---|---|---|---|---|---|---|
| 1 | rHVT/CMVH5Wis68 | CMV (Ex[2]) | One-day-old | 1638 | SQ[3] | 17 |
| 2 | rHVT/CMVH5Wis68 | CMV (Ex) | One-day-old | 375 | SQ | 17 |
| 3 | rHVT/PecH5Wis68 | Pec (CE[4]) | One-day-old | 2800 | SQ | 17 |
| 4 | rHVT/PecH5Wis68 | Pec (CE) | One-day-old | 550 | SQ | 17 |
| 5 | rHVT/BacH5Wis68 | Bac (CE) | One-day-old | 4350 | SQ | 17 |
| 6 | rHVT/BacH5Wis68 | Bac (CE) | One-day-old | 720 | SQ | 17 |
| 7 | Inactivated H5N9 vaccine | N/A[5] | 3-weeks-old | 0.5 ml[6] | SQ | 17 |
| 8 | Negative controls | N/A | N/A | None | N/A | 10 | pfu[1] = plaque forming units
Ex[2] = example
SQ[3] = subcutaneous
CE[4] = comparative example
N/A[5] = not applicable
ml[6] = milliliter

TABLE 3

HI titers

| Group # | 3 weeks Positive[1]/Total | 3 weeks GMT titer[2] | 4 weeks Positive/Total | 4 weeks GMT titer | 5 weeks Positive/Total | 5 weeks GMT titer | 6 weeks Positive/Total | 6 weeks GMT titer | 7 weeks Positive/Total | 7 weeks GMT titer |
|---|---|---|---|---|---|---|---|---|---|---|
| 1 | 16/17 (94%) | 23.5 | 15/17 (88%) | 47.1 | 17/17 (100%) | 62.6 | 17/17 (100%) | 94.2 | 17/17 (100%) | 70.8 |
| 2 | 14/17 (82%) | 18.4 | 17/17 (100%) | 47.1 | 17/17 (100%) | 53.2 | 16/16 (100%) | 113.1 | 16/16 (100%) | 118.1 |
| 3 | 15/17 (88%) | 17.7 | 16/17 (94%) | 24.5 | 16/17 (94%) | 28.9 | 17/17 (100%) | 38.4 | 16/17 (94%) | 47.1 |
| 4 | 14/17 (82%) | 23.5 | 16/17 (94%) | 28.9 | 15/17 (88%) | 23.5 | 13/17 (76%) | 23.2 | 14/17 (82%) | 28.9 |
| 5 | 16/17 (94%) | 35.4 | 16/17 (94%) | 32.6 | 15/17 (88%) | 25.5 | 14/17 (82%) | 21.4 | 13/17 (76%) | 28.5 |

TABLE 3-continued

HI titers

| Group # | 3 weeks Positive[1]/Total | 3 weeks GMT titer[2] | 4 weeks Positive/Total | 4 weeks GMT titer | 5 weeks Positive/Total | 5 weeks GMT titer | 6 weeks Positive/Total | 6 weeks GMT titer | 7 weeks Positive/Total | 7 weeks GMT titer |
|---|---|---|---|---|---|---|---|---|---|---|
| 6 | 11/17 (65%) | 11.0 | 11/17 (65%) | 11.6 | 12/17 (71%) | 9.5 | 10/17 (59%) | 13.9 | 10/16 (63%) | 10.9 |
| 7 | N/A[3] | N/A | N/A | N/A | N/A | N/A | 17/17 (100%) | 294.9 | 17/17 (100%) | 461.9 |
| 8 | 0/10 (0%) | N/A | 0/10 (0%) | N/A | 0/10 (0%) | N/A | 0/10 (0%) | N/A | 0/10 (0%) | N/A |

Positive[1] = HI titers of equal to or more than 10 were considered positive.
GMT titer[2] = Geometric mean titer
N/A[3] = not applicable

TABLE 4

Treatment groups for the second serological evaluation

| Group # | Treatment Group | Promoters | Age of vaccination | Vaccine dose (pfu[1]) | Vaccine route | # of chickens |
|---|---|---|---|---|---|---|
| 1 | rHVT/CMVH5Wis68 | CMV (Ex[2]) | 18-day old embryos | 980 | In ovo | 18 |
| 2 | rHVT/CMVH5Wis68 | CMV (Ex) | One-day-old | 695 | SQ[3] | 10 |
| 3 | rHVT/BacH5Wis68 | Bac (CE[4]) | One-day-old | 1155 | SQ | 10 |
| 4 | Negative controls | N/A[5] | N/A | None | N/A | 10 | pfu[1] = plaque forming units
Ex[2] = example
SQ[3] = subcutaneous
CE[4] = comparative example
N/A[5] = not applicable

TABLE 5

HI titers for the second serological evaluation

| Group # | 2 weeks Positive[1]/Total | 2 weeks GMT titer[2] | 3 weeks Positive/Total | 3 weeks GMT titer | 4 weeks Positive/Total | 4 weeks GMT titer | 5 weeks Positive/Total | 5 weeks GMT titer | 6 weeks Positive/Total | 6 weeks GMT titer | 7 weeks Positive/Total | 7 weeks GMT titer |
|---|---|---|---|---|---|---|---|---|---|---|---|---|
| 1 | 12/18 (67%) | 8.3 | 18/18 (100%) | 66.0 | 18/18 (100%) | 83.1 | 18/18 (100%) | 148.1 | 18/18 (100%) | 201.6 | 18/18 (100%) | 179.6 |
| 2 | 9/10 (90%) | 17.0 | 10/10 (100%) | 105.6 | 10/10 (100%) | 171.5 | 10/10 (100%) | 91.9 | 10/10 (100%) | 105.6 | 10/10 (100%) | 80.0 |
| 3 | 7/10 (70%) | 7.1 | 10/10 (100%) | 45.9 | 10/10 (100%) | 65.0 | 10/10 (100%) | 211.1 | 10/10 (100%) | 60.6 | 10/10 (100%) | 49.2 |
| 4 | 0/10 (0%) | N/A[3] | 0/10 (0%) | N/A | 0/10 (0%) | N/A | 0/10 (0%) | N/A | 0/10 (0%) | N/A | 0/10 (0%) | N/A |

Positive[1] = HI titers of equal to or more than 10 were considered positive.
GMT titer[2] = Geometric mean titer
N/A[3] = not applicable

TABLE 6

Treatment groups for the efficacy trial against highly pathogenic avian influenza virus

| Group # | Treatment Group | Promoters | Age of vaccination | Vaccine dose (pfu[1]) | Vaccine route | # of chickens |
|---|---|---|---|---|---|---|
| 1 | rHVT/CMVH5Wis68 | CMV (Ex[2]) | One-day-old | 1075 | SQ[3] | 20 |
| 2 | rHVT/BacH5Wis68 | Bac (CE[4]) | One-day-old | 1080 | SQ | 20 |

TABLE 6-continued

Treatment groups for the efficacy trial against highly pathogenic avian influenza virus

| Group # | Treatment Group | Promoters | Age of vaccination | Vaccine dose (pfu[1]) | Vaccine route | # of chickens |
|---|---|---|---|---|---|---|
| 3 | Challenge controls | N/A[5] | N/A | None | N/A | 20 |
| 4 | Negative controls | N/A | N/A | None | N/A | 5 | pfu[1] = plaque forming units
Ex[2] = example
SQ[3] = subcutaneous
CE[4] = comparative example
N/A[5] = not applicable

TABLE 7

Protection of recombinant HVT against highly pathogenic avian influenza virus

| Group # | Treatment Group | # protected/total | % protection |
|---|---|---|---|
| 1 | rHVT/CMVH5Wis68 | 19/20 | 95% |
| 2 | rHVT/BacH5Wis68 | 13/20 | 65% |
| 3 | Challenge controls | 0/10 | 0% |
| 4 | Negative controls | 5/5 | 100% |

The invention claimed is:

1. A recombinant turkey herpesvirus comprising a hemagglutinin gene of an avian influenza virus and a cytomegalovirus immediate early promoter, wherein said hemagglutinin gene is under control of said cytomegalovirus immediate early promoter and wherein said hemagglutinin gene and said cytomegalovirus immediate early promoter are present between UL45 and UL46 of the turkey herpesvirus genome.

2. A poultry vaccine comprising the recombinant turkey herpesvirus according to claim 1.

3. A method for vaccinating poultry against avian influenza, comprising administering to a poultry the recombinant turkey herpesvirus according to claim 1.

4. The method of claim 3, wherein said poultry is chicken.

* * * * *